(12) United States Patent
Dinsmoor et al.

(10) Patent No.: US 11,779,765 B2
(45) Date of Patent: *Oct. 10, 2023

(54) POSTURE-BASED CONTROL OF ELECTRICAL STIMULATION THERAPY

(71) Applicant: Medtronic, Inc., Minneapolis, MN (US)

(72) Inventors: David A. Dinsmoor, North Oaks, MN (US); Christopher L. Pulliam, Plymouth, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 21 days.

This patent is subject to a terminal disclaimer.

(21) Appl. No.: 17/556,203

(22) Filed: Dec. 20, 2021

(65) Prior Publication Data

US 2022/0111210 A1   Apr. 14, 2022

Related U.S. Application Data

(63) Continuation of application No. 16/721,528, filed on Dec. 19, 2019, now Pat. No. 11,202,912.

(51) Int. Cl.
*A61N 1/36* (2006.01)
*A61B 5/11* (2006.01)
(Continued)

(52) U.S. Cl.
CPC ........ *A61N 1/36135* (2013.01); *A61B 5/1116* (2013.01); *A61N 1/025* (2013.01);
(Continued)

(58) Field of Classification Search
CPC ............ A61N 1/36135; A61N 1/36125; A61N 1/025; A61N 1/36139; A61N 1/36031;
(Continued)

(56) References Cited

U.S. PATENT DOCUMENTS 8,515,549 B2    8/2013  Panken et al.
8,918,177 B2   12/2014  Gauthier
(Continued)

FOREIGN PATENT DOCUMENTS

CN    105792745 A    7/2016
EP      3024540 B1   6/2016
(Continued)

OTHER PUBLICATIONS

International Search Report and Written Opinion of International Application No. PCT/US2020/060327, dated Feb. 17, 2021, 10 pp.
(Continued)

*Primary Examiner* — Paula J Stice
(74) *Attorney, Agent, or Firm* — Shumaker & Sieffert, P.A.

(57) ABSTRACT

Devices, systems, and techniques are described for selecting an evoked compound action potential (ECAP) growth curve based on a posture of a patient. The ECAP growth curve defines a relationship between a parameter defining delivery of stimulation pulses delivered to the patient and a parameter of an ECAP signal of a nerve of a patient elicited by a stimulation pulse. In one example, a medical device detects a posture of a patient and selects an ECAP growth curve corresponding to the detected posture. The medical device selects, based on the ECAP growth curve corresponding to the detected posture and a characteristic of a detected ECAP signal, a value for a parameter for defining delivery of the stimulation pulses to the patient and controls delivery of the stimulation pulses according to the selected value for the parameter.

20 Claims, 10 Drawing Sheets

(51) Int. Cl.
    *A61N 1/02*     (2006.01)
    *A61N 1/372*     (2006.01)

(52) U.S. Cl.
    CPC ...... *A61N 1/36125* (2013.01); *A61N 1/36031* (2017.08); *A61N 1/36139* (2013.01); *A61N 1/37247* (2013.01)

(58) Field of Classification Search
    CPC .. A61N 1/36062; A61N 1/0551; A61B 5/1116
    See application file for complete search history.

(56) References Cited

U.S. PATENT DOCUMENTS

| | | |
|---|---|---|
| 8,958,885 B2 | 2/2015 | Panken et al. |
| 9,084,900 B2 | 7/2015 | Hershey et al. |
| 9,302,112 B2 | 4/2016 | Bernzin et al. |
| 9,381,356 B2 | 7/2016 | Parker et al. |
| 9,511,231 B1 | 12/2016 | Kent et al. |
| 9,553,148 B2 | 1/2017 | Carcieri |
| 10,183,168 B2 | 1/2019 | Baru et al. |
| 10,327,654 B2 | 6/2019 | Strahl et al. |
| 11,179,567 B2 | 11/2021 | Dinsmoor et al. |
| 11,202,912 B2 | 12/2021 | Dinsmoor et al. |
| 2014/0236257 A1 | 8/2014 | Parker et al. |
| 2014/0277282 A1 | 9/2014 | Jaax |
| 2015/0032181 A1 | 1/2015 | Baynham et al. |
| 2015/0173636 A1 | 6/2015 | Mokelke et al. |
| 2015/0360031 A1 | 12/2015 | Bornzin et al. |
| 2016/0157769 A1 | 6/2016 | Min et al. |
| 2016/0287126 A1 | 10/2016 | Parker et al. |
| 2016/0339251 A1 | 11/2016 | Kent et al. |
| 2017/0135624 A1 | 5/2017 | Parker |
| 2017/0361101 A1 | 12/2017 | Single |
| 2018/0110987 A1 | 4/2018 | Parker |
| 2018/0126169 A1 | 5/2018 | Hou et al. |
| 2019/0168000 A1 | 6/2019 | Laird-Wah |
| 2019/0209844 A1 | 7/2019 | Esteller et al. |
| 2020/0046980 A1 | 2/2020 | Moffitt et al. |
| 2021/0187298 A1 | 6/2021 | Dinsmoor et al. |
| 2021/0187299 A1 | 6/2021 | Dinsmoor et al. |
| 2021/0187300 A1 | 6/2021 | Dinsmoor et al. |

FOREIGN PATENT DOCUMENTS

| | | |
|---|---|---|
| JP | 2018513714 A | 5/2018 |
| WO | 2012155188 A1 | 11/2012 |
| WO | 2015070281 A1 | 5/2015 |
| WO | 2016011512 A1 | 1/2016 |
| WO | 2016090436 A1 | 6/2016 |
| WO | 2017100866 A1 | 6/2017 |
| WO | 2017173493 A1 | 10/2017 |
| WO | 2017219096 A1 | 12/2017 |
| WO | 2019204884 A1 | 10/2019 |

OTHER PUBLICATIONS

Laird-Wah, "Improving Spinal Cord Stimulation—Model-Based Approaches to Evoked Response Telemetry," Dissertation submitted to the University of South Wales, Aug. 2015, 273 pp.

Prosecution History from U.S. Appl. No. 16/721,528, now issued U.S. Pat. No. 11,202,912, dated Dec. 19, 2019 through Dec. 2, 2021, 230 pp.

Shariati et al., "Evaluating Spinal Cord Stimulation Incorporating Feedback Control Using Evoked Compound Action Potential," Saluda Medical, Dec. 2, 2014, 1 pp.

U.S. Appl. No. 17/456,123, filed Nov. 22, 2021, naming inventors Dinsmoor et al.

POSTURE-BASED CONTROL OF ELECTRICAL STIMULATION THERAPY

This application is a continuation of U.S. patent application Ser. No. 16/721,528, filed Dec. 19, 2019, the entire contents of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation therapy may be delivered by the medical device in a train of electrical stimulation pulses. Stimulation parameters that define the electrical stimulation pulses may include a frequency, an amplitude, a pulse width, and a pulse shape. The parameters of the electrical stimulation pulses may be altered in response to user input or sensory input.

SUMMARY

Systems, devices, and techniques are described for selecting a target evoked compound action potential (ECAP) characteristic value based on a detected posture of a patient, where the target ECAP characteristic value may be selected from a respective ECAP growth curve corresponding to the detected posture. The system may use the target ECAP characteristic value to control electrical stimulation therapy delivered to the patient. An ECAP growth curve defines a relationship between a parameter defining delivery of electrical stimulation pulses delivered to the patient and a characteristic of an ECAP signal of a nerve of a patient elicited by the electrical stimulation pulses. In some examples, ECAP signals can be detected from the stimulation pulses delivered to provide therapy to the patient. In other examples, stimulation pulses (e.g., informed stimulation pulses) configured to provide therapeutic effect for the patient may not allow ECAP signals to be detected. Therefore, the system may deliver control stimulation pulses to elicit a detectable ECAP response from a tissue of the patient. The ECAP response of the patient is sensed, and characteristics of the sensed ECAP are used to inform the selection of one or more parameters defining the informed stimulation pulses delivered to the patient. Informed stimulation pulses typically are configured to contribute a therapeutic effect to the patient. Control stimulation pulses may contribute to a therapeutic effect for the patient, provide a therapeutic effect substantially less than the informed stimulation pulses, or not provide any therapeutic effect to the patient. Control stimulation pulses and informed stimulation pulses may be at least partially interleaved with each other. A therapeutic effect may include paresthesia that relieves pain symptoms by covering painful sensations or directly reducing pain perceived by the patient. Control stimulation pulses are those stimulation pulses that are configured as ECAP test pulses to elicit a detectable ECAP signal that may, or may not, have the primary purpose of contributing to the therapy for the patient. Informed stimulation pulses are those stimulation pulses that do not elicit a detectable ECAP signal.

In one example, a medical device detects a posture of a patient. The medical device selects an ECAP growth curve corresponding to the detected posture. One or more control stimulation pulses can be delivered to the patient, and the system may sense the resulting ECAP signal. The medical device selects, based on the ECAP growth curve corresponding to the detected posture and the sensed ECAP signal, a value for a parameter that at least partially defines delivery of the control stimulation pulses and/or a parameter that at least partially defines delivery of the informed stimulation pulses to the patient.

The medical device may control delivery of the informed stimulation pulses according to the selected value for the stimulation parameter. For example, in response to determining that a characteristic value of the ECAP signal (e.g., a voltage amplitude) has deviated from a target ECAP characteristic value of the ECAP growth curve, the system may change one or more stimulation parameters of the next one or more informed stimulation pulses to be delivered to the patient. For example, the system may increase or decrease a current amplitude of the informed stimulation pulses by a predetermined step size or based on a gain value representative of the selected growth curve for the patient. In this manner, the system may be configured to maintain a consistent volume of neural activation by adjusting the one or more stimulation parameters of the control stimulation pulses and/or informed stimulation pulses, depending on what types of stimulation pulses are used for the therapy.

In one example, this disclosure describes a method comprising: detecting, by one or more processors of a medical device and via one or more sensors, a posture of a plurality of postures of the patient; selecting, by the one or more processors and based on the detected posture, an evoked compound action potential (ECAP) growth curve of a plurality of ECAP growth curves, wherein each ECAP growth curve of the plurality of ECAP growth curves is associated with at least one posture of the plurality of postures, and wherein each ECAP growth curve of the plurality of ECAP growth curves defines a relationship between a parameter defining delivery of one or more stimulation pulses to a patient and a characteristic of an ECAP signal elicited by a control stimulation pulse; selecting, by the one or more processors and based on the selected ECAP growth curve, a value of a target ECAP characteristic; comparing the value of the target ECAP characteristic to a value of the characteristic of the ECAP signal elicited by the control stimulation pulse; selecting, by the one or more processors and based on the comparison, a value for the parameter defining delivery of the one or more stimulation pulses to the patient; and controlling, by the one or more processors, delivery of the one or more stimulation pulses according to the selected value for the parameter.

In another example, this disclosure describes a system comprising: one or more sensors; a medical device comprising therapy delivery circuitry configured to deliver therapy to a patient; and processing circuitry configured to: detect, via the one or more sensors, a posture of a plurality of postures of the patient; select, based on the detected posture, an evoked compound action potential (ECAP) growth curve of a plurality of ECAP growth curves, wherein each ECAP growth curve of the plurality of ECAP growth curves is associated with at least one posture of the plurality of postures, and wherein each ECAP growth curve of the plurality of ECAP growth curves defines a relationship between a parameter defining delivery of one or more stimulation pulses to a patient and a characteristic of an ECAP signal elicited by a control stimulation pulse; select, based on the selected ECAP growth curve, a value of a target ECAP characteristic; compare the value of the target ECAP characteristic to a value of the characteristic of the ECAP signal elicited by the control stimulation pulse; select, based on the comparison, a value for the parameter defining delivery of the one or more stimulation pulses to the patient; and control the therapy delivery circuitry of the medical device to deliver the one or more stimulation pulses according to the selected value for the parameter.

In another example, this disclosure describes a non-transitory, computer-readable medium comprising instructions that, when executed, cause processing circuitry of a medical device to: detect, via one or more sensors, a posture of a plurality of postures of the patient; select, based on the detected posture, an evoked compound action potential (ECAP) growth curve of a plurality of ECAP growth curves, wherein each ECAP growth curve of the plurality of ECAP growth curves is associated with at least one posture of the plurality of postures, and wherein each ECAP growth curve of the plurality of ECAP growth curves defines a relationship between a parameter defining delivery of one or more stimulation pulses to a patient and a characteristic of an ECAP signal elicited by a control stimulation pulse; select, based on the selected ECAP growth curve, a value of a target ECAP characteristic; compare the value of the target ECAP characteristic to a value of the characteristic of the ECAP signal elicited by the control stimulation pulse; select, based on the comparison, a value for the parameter defining delivery of the one or more stimulation pulses to the patient; and control delivery of the one or more stimulation pulses according to the selected value for the parameter.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
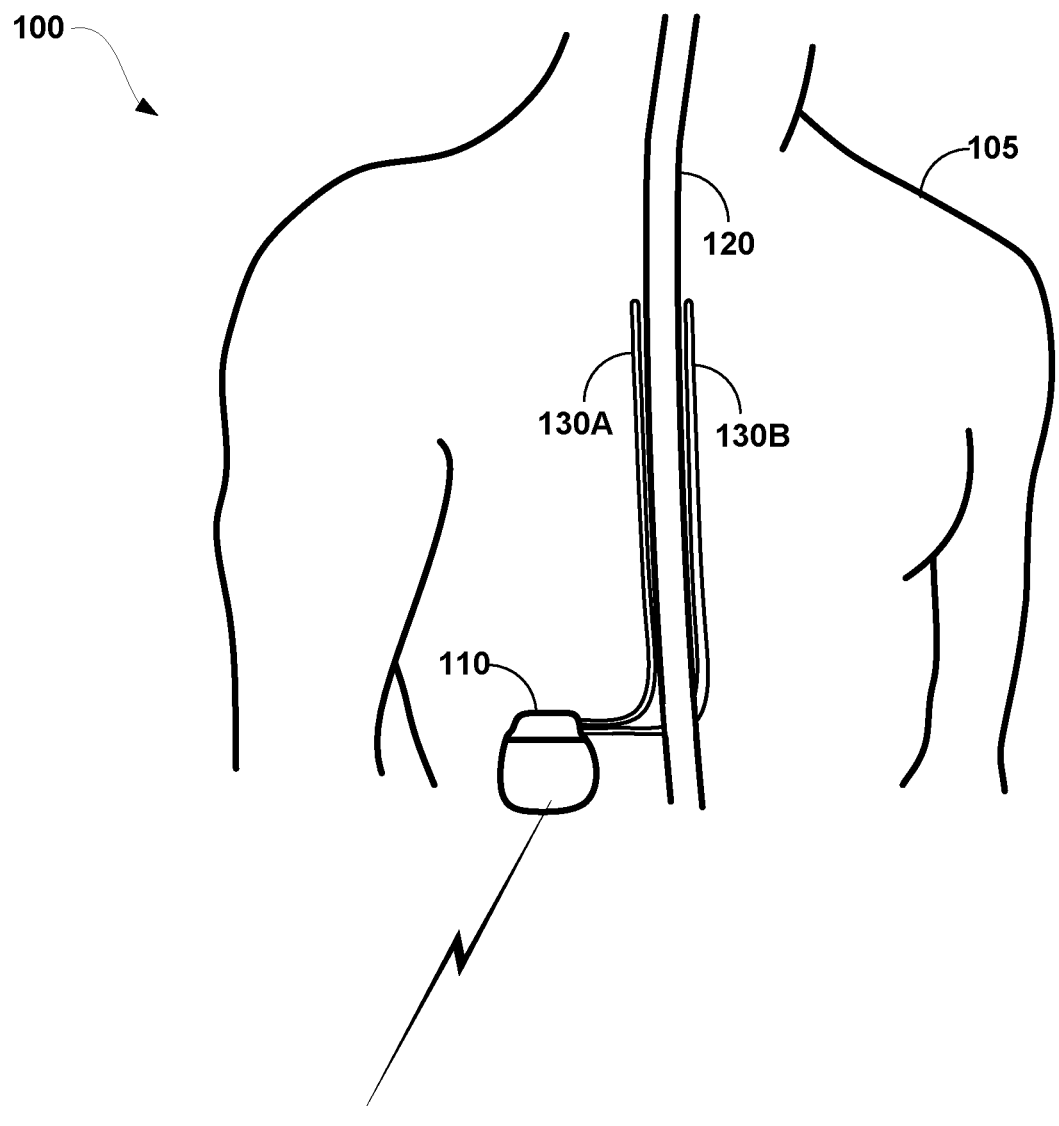
FIG. 1 is a conceptual diagram illustrating an example system that includes a medical device programmer and an implantable medical device (IMD) configured to deliver spinal cord stimulation (SCS) therapy according to the techniques of the disclosure.

The disclosure describes examples of medical devices, systems, and techniques for automatically adjusting electrical stimulation therapy delivered to a patient based on one or more characteristics of evoked compound action potentials (ECAPs). The ECAP may be identified by a medical device in response to a stimulation pulse delivered by the medical device. Electrical stimulation therapy is typically delivered to a target tissue (e.g., one or more nerves or muscle) of a patient via two or more electrodes. Stimulation parameters that define pulses of the electrical stimulation therapy (e.g., electrode combination, voltage or current amplitude, pulse width, pulse frequency, pulse shape, etc.) can be selected by a clinician and/or the patient to provide relief from various symptoms, such as pain, muscle disorders, etc. However, as the patient moves, the distance between the electrodes and the target tissue (e.g., targeted nerves and/or muscles) changes. Since neural recruitment is a function of stimulation intensity and distance between the target tissue and the electrodes, movement of the electrode closer to the target tissue may result in increased perception by the patient (e.g., possible painful sensations), and movement of the electrode further from the target tissue may result in decreased efficacy of the therapy for the patient.

ECAPs are a measure of neural recruitment because each ECAP signal represents the superposition of electrical potentials generated from axons firing in response to an electrical stimulus (e.g., a stimulation pulse). Characteristics (e.g., an amplitude of a portion of the signal) of an ECAP signal occur as a function of how many axons (and what types of nerve fibers) have been activated by the delivered stimulation pulse. A system can monitor changes in values of one or more characteristics of the ECAP signal and use that change in a characteristic value to adjust one or more stimulation parameter that defines stimulation pulses delivered to the patient. For example, the system can reduce the intensity of stimulation pulses (e.g., reduce a current amplitude and/or pulse width) in response to detecting an increase in an amplitude of an ECAP signal.

Nerve impulses are detectable as an ECAP signal that travels quickly along nerve fibers in response to a delivered stimulation pulse that depolarizes the nerves. The ECAP signal typically has a smaller amplitude than the delivered stimulation pulse. Therefore, if the delivered stimulation pulse delivered by first electrodes has a pulse width that is too long, different electrodes configured to sense the ECAP may sense the delivered stimulation pulse itself as an artifact that obscures at least a portion of the ECAP signal. Additionally, the ECAP signal loses fidelity as the electrical potentials propagate along nerve fibers from the tissue site of the electrical stimulus because different nerve fibers propagate electrical potentials at different speeds. Therefore, sensing the ECAP at a far distance from the stimulating electrodes may reduce the occurrence of an artifact caused by a stimulation pulse with a long pulse width. However, the ECAP signal may lose the fidelity needed to detect changes to characteristic values of the ECAP signal that occur when the electrode-to-target tissue distance changes. In other words, for certain stimulation pulses having relatively longer pulse widths, the system may be unable to identify, at any distance from the stimulation electrodes, ECAPs resulting from the certain stimulation pulses such that the identified ECAPs may be used to control therapy to the patient.

As described herein, a medical device may be configured to deliver a plurality of stimulation pulses, detect ECAP signals from at least some of the stimulation pulses, determine a respective posture of the patient at the time the ECAP signals were detected, and adjust subsequent stimulation pulses based on a characteristic value of the detected ECAP signals relative to a target ECAP characteristic value specific to the respective posture determined during the detected ECAP signals. In some examples, this technique may be applied to situations in which the medical device delivers informed stimulation pulses, from which ECAP signals cannot be detected, and control stimulation pulses configured to elicit detectable ECAP signals.

For example, the medical device may deliver control stimulation pulses configured to elicit a detectable ECAP signal from the patient. The control stimulation pulses may be interleaved with delivery of a plurality of informed stimulation pulses. For example, the medical device may alternate the delivery of control stimulation pulses with informed stimulation pulses such that a control stimulation pulse is delivered, and an ECAP signal is sensed, between consecutive informed stimulation pulses from which ECAP signals cannot be detected. In some examples, multiple control stimulation pulses are delivered, and respective ECAP signals sensed, between the delivery of consecutive informed stimulation pulses. In some examples, multiple informed stimulation pulses will be delivered between consecutive control stimulation pulses. In some examples, either the control stimulation pulses, the informed stimulation pulses, or both the control stimulation pulses and informed stimulation pulses are a plurality of electrical stimulation pulses configured to provide a therapy to the patient. In some examples, either the control stimulation pulses, the informed stimulation pulses, or both the control stimulation pulses and informed stimulation pulses are a plurality of electrical stimulation pulses configured to be delivered without the primary purpose of providing a therapy to the patient. In some examples, the plurality of electrical stimulation pulses configured to provide the therapy to the patient are at least partially interleaved with the plurality of electrical stimulation pulses configured to be delivered without the primary purpose of providing a therapy to the patient. In this manner, as described herein, the control stimulation pulses and the informed stimulation pulses may, or may not, contribute to a therapeutic effect for the patient. If control stimulation pulses contribute to a therapeutic effect, a medical device may deliver only control stimulation pulses without delivering informed stimulation pulses (e.g., without pulses from which ECAP signals cannot be detected).

In any case, one or more informed stimulation pulses may be delivered according to a predetermined pulse frequency selected so that the informed stimulation pulses can produce a therapeutic result for the patient. One or more control stimulation pulses are then delivered, and the respective ECAP signals sensed, within one or more time windows between consecutive informed stimulation pulses delivered according to the predetermined pulse frequency. In this manner, a medical device can administer therapy to the patient uninterrupted while ECAPs are sensed during times at which the informed stimulation pulses are not being delivered.

The system may adjust one or more parameters that at least partially define the informed stimulation pulses in response to determining changes to one or more characteristics of the sensed ECAP signals elicited by the control stimulation pulses. For instance, the medical device may measure a characteristic value (such as an amplitude) of the ECAP signal elicited by a control stimulation pulse and compare it to a target ECAP characteristic value previously identified as appropriate for the patient. As an example where the characteristic value of the ECAP signal is an amplitude of the ECAP signal, if the amplitude of the ECAP signal (e.g. a voltage amplitude of one or more peaks in the ECAP signal) is greater than a target ECAP amplitude, then the intensity of the control stimulation pulses may be too high because the stimulation electrodes have moved closer to the nerves. The medical device may responsively reduce the intensity (e.g., current amplitude, pulse width, pulse frequency, slew rate, or any combination thereof) of the informed stimulation pulses. Conversely, if the amplitude of the ECAP signal is less than the target ECAP amplitude, then the intensity of the control stimulation pulses may not be strong enough because the stimulation electrodes have moved farther from the nerves. The medical device may responsively increase the intensity of the informed stimulation pulses. In this manner, the medical device may monitor the ECAP signal elicited from the control stimulation pulses to adjust one or more parameters of informed stimulation pulses to maintain a volume of neural activation that provides efficacious therapy for the patient.

The pulse width of the control stimulation pulses may be shorter than the pulse width of the informed stimulation pulses to reduce or prevent a sensed electrical artifact from control stimulation pulses from obscuring or otherwise interfering with the detected of the ECAP signals. For example, the control stimulation pulses may be less than approximately 300 microseconds (μs). In one example, the control stimulation pulse may be a bi-phasic pulse having a positive phase of approximately 100 μs and a negative phase of approximately 100 μs separated by an interphase interval of approximately 30 μs. In this manner, stimulation electrodes at one end of a lead may deliver the control stimulation pulse and electrodes at the other end of the same lead may sense the ECAP signal without, or with minimal, interference from the control stimulation pulse itself. The control stimulation pulses may, or may not, contribute to a therapeutic effect for the patient.

In one example, a system may adjust one or more parameters of informed stimulation pulses based on one or more characteristics of sensed ECAP signals. The medical device may determine a characteristic value (e.g., such as an amplitude) of at least one respective ECAP signal. The medical device may then compare the characteristic value to a target ECAP characteristic value (e.g., a target ECAP amplitude) and a target ECAP adjustment window. For example, the target ECAP adjustment window may be a range of amplitudes around the target ECAP amplitude, including an upper-bound and a lower-bound. In some examples, the target ECAP adjustment window may be defined by the target ECAP characteristic value plus and minus a variance so that adjustments are not made to the one or more parameters of the informed stimulation pulses for minor oscillations in the ECAP signal. In other words, the target ECAP characteristic value plus the variance may be the upper-bound of the target ECAP adjustment window, and the target ECAP characteristic value minus the variance may be the lower-bound of the target ECAP adjustment window. The variance may be the same or different above and below the target ECAP characteristic value. If the representative amplitude of the at least one respective ECAP is greater than the upper-bound of the target ECAP adjustment window, then the medical device may be configured to decrease the amplitude of subsequent informed stimulation pulses and the control stimulation pulses. The control stimulation pulses may also be adjusted in order to determine if further adjustments are needed based on subsequently detected ECAP signals. If the representative amplitude of the at least one respective ECAP is lower than the lower-bound of the target ECAP adjustment window, then the medical device may be configured to increase the amplitude of the informed stimulation pulses and the control stimulation pulses following the at least one respective ECAP. The amount that the amplitude of the informed stimulation pulses and the control stimulation pulses is changed may be a predetermined amplitude step size or a predetermined percentage based on the detected change in the representative amplitude of the ECAP signal. In this manner, the feedback loop may take more than one iteration to achieve the target ECAP amplitude once again.

In some examples, the medical device may employ a dynamic feedback loop. A growth curve may be determined for the patient that is determined based on the slope of the relationship between detected values of a characteristic of ECAP signals for respective different stimulation pulse amplitudes. Therefore, the medical device may determine a difference between the target ECAP characteristic value (e.g., an amplitude value) and a measured ECAP value and multiply the difference by the gain value defined by the growth curve. The resulting value can then be used to increase or decrease the previous parameter value that defined the control stimulation pulse that resulted in the measured ECAP value. The gain value can also be used to similarly adjust the parameter values of the informed stimulation pulses. By employing the gain value, the system may be able to respond quickly to large ECAP signal variations and reset the control stimulation pulses and informed stimulation pulses to the target ECAP.

Furthermore, in accordance with the techniques of the disclosure, the medical device detects a posture of the patient and selects a growth curve of a plurality of growth curves that corresponds to the detected posture of the patient. As discussed above, neural recruitment (e.g., an ECAP response) is a function of stimulation intensity and distance between the target tissue and the stimulating electrodes. However, the distance between the stimulating electrodes and the target tissue may change as a patient assumes different postures. For example, as a patient changes posture and the position of the stimulating electrodes relative to the target tissue changes, movement of the stimulating electrodes closer to the target tissue may result in increased perception by the patient (e.g., possible painful sensations), and movement of the electrode further from the target tissue may result in decreased efficacy of the therapy for the patient. Thus, a parameter defining the stimulation pulses that provides effective therapy with few side effects to the patient while the patient is in a first posture may not provide effective therapy or may increase the occurrence of side effects experienced by the patient while the patient is in a second posture. A medical device operating in accordance with the techniques of the disclosure may select a growth curve that corresponds to a detected posture of the patient such that the medical device may use a target ECAP characteristic value for controlling electrical stimulation therapy that is selected from the growth curve corresponding to the detected posture of the patient. This process may reduce the number of informed stimulation pulses that produce less effective therapy resulting from electrode-to-tissue distance changes during patient movement or changes in posture.

Control stimulation pulses and informed stimulation pulses are generally described herein as different stimulation pulses reflective of different types of electrical stimulation. However, the different types of electrical stimulation, and their respective pulses, may be described with different attributes. For example, a first type of electrical stimulation may include first pulses configured to primarily contribute to a therapy for a patient (e.g., informed stimulation pulses). The first pulses of this first type of electrical stimulation may also have one or more parameters (e.g., a pulse width) that prevent or reduce the ability of the system to detect ECAP signals elicited from the first pulses of the first type of electrical stimulation because an artifact representative of the first pulses themselves overlaps with and obscures at least a portion of the respective elicited ECAP signal. When a system delivers pulses of a first type, a second type of electrical stimulation may include second pulses defined by one or more parameter values selected to elicit ECAP signals that are sensed and detectable by the system. The second pulses may thus be referred to as "control stimulation pulses," "sense pulses," or "test pulses" since the second pulses are configured to elicit a detectable ECAP signal. For example, the second pulses of the second type of electrical stimulation may improve the detectability of the ECAP signal such as to not generate an artifact that obscures the ECAP signals or otherwise prevents or reduces the ability of the system to detect the ECAP signal from each of the second pulses. In addition, the second pulses may be defined by parameter values selected to elicit an ECAP signal that is used to at least modify one or more parameter values of the first pulses of the first type of electrical stimulation. The first pulses may thus differ from the second pulses by at least one parameter (e.g., current and/or voltage amplitude, pulse width, and/or frequency). The first pulses may be at least partially interleaved with at least some of the second pulses. For example, the system may alternate delivery of one first pulse with delivery of one second pulse. In another example, the number of first pulses may differ from the number of second pulses by a ratio or percentage. The ratio could be 1:1 when the first and second pulses are fully interleaved. The ratio could be 10:1 first pulses to second pulses in examples in which the second pulses are delivered less frequently than the first pulses. In other examples, the ratio could be 1:4 first pulses to second pulses when the second pulses, and respective sensed ECAP signals) occur more frequently than the first pulses. The second pulses may or may not contribute to a therapy or sensation perceived by the patient, but the primary purpose of the second pulses is to elicit respective ECAP signals that are detectable by the system separate from any sensed artifacts representative of the second pulses themselves.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating example system 100 that includes implantable medical device (IMD) 110 configured to deliver electrical stimulation therapy to patient 105. In the example shown in FIG. 1, IMD 110 is configured to deliver spinal cord stimulation (SCS) therapy according to the techniques of the disclosure. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In addition to electrical stimulation therapy, IMD 110 may also be configured to generate and deliver control stimulation pulses configured to elicit ECAP signals, where the control stimulation pulses may or may not contribute to a therapeutic effect for the patient. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2A) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 may be selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

An ECAP test stimulation program may define stimulation parameter values that define control stimulation pulses delivered by IMD 110 through at least some of the electrodes of leads 130. These stimulation parameter values may include information identifying which electrodes have been selected for delivery of the control stimulation pulses, the polarities of the selected electrodes, e.g., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program may define when the control stimulation pulses are to be delivered to the patient based on the frequency and/or pulse width of the control stimulation pulses. The control stimulation pulses defined by each ECAP test stimulation program may or may not be intended to provide or contribute to therapy for the patient.

The stimulation parameters of a therapy stimulation program that defines the informed stimulation pulses of electrical stimulation therapy by IMD 110 through the electrodes of leads 130 may include information identifying which electrodes have been selected for delivery of stimulation according to a stimulation program, the polarities of the selected electrodes, e.g., the electrode combination for the program, and voltage or current amplitude, pulse frequency, pulse width, pulse shape of stimulation delivered by the electrodes. These stimulation parameters of stimulation pulses are typically predetermined parameter values determined prior to delivery of the stimulation pulses. However, in some examples, system 100 may change one or more parameter values automatically based on one or more factors or based on user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 may include one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy. In some examples, the electrical stimulation therapy may include control stimulation pulses that elicit detectable ECAP signals and, in some cases, informed stimulation pulses that do not elicit detectable ECAP signals. Informed stimulation pulses may generally be described as therapy pulses or pulses that contribute to the therapeutic effect for a patient, and control stimulation pulses may, or may not (e.g., non-therapeutic pulses), contribute to therapeutic effect for the patient. In other words, IMD 110 may deliver control stimulation pulses in addition to informed stimulation pulses when IMD 110 cannot detect ECAP signals from the informed stimulation pulses configured to provide therapy to the patient. For example, IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

Furthermore, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted to receive stimulation therapy. IMD 110 may deliver control stimulation pulses via the same, at least some of the same, or different electrodes as those used to deliver informed stimulation pulses (when informed stimulation pulses are part of the therapy program). Put another way, control stimulation pulse may be delivered without informed stimulation pulses when the patient receives a therapeutic effect from the control stimulation pulses.

Since control stimulation pulses are delivered in an interleaved manner with informed stimulation pulses when both control and informed stimulation pulses are delivered, a clinician and/or user may select any desired electrode combination for informed stimulation pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control stimulation pulse may include an imbalanced bi-phasic portion and a passive recharge portion. Although not necessary, a bi-phasic control stimulation pulse may include an interphase interval between the positive and negative phase to promote propagation of the nerve impulse in response to the first phase of the bi-phasic pulse. The control stimulation may be delivered without interrupting the delivery of the electrical stimulation informed stimulation pulses, such as during the window between consecutive informed stimulation pulses. The control stimulation pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 delivers control stimulation pulses to a target stimulation site within patient 105 via the electrodes of leads 130 according to one or more ECAP test stimulation programs. The one or more ECAP test stimulation programs may be stored in a memory of IMD 110. Each ECAP test program of the one or more ECAP test stimulation programs includes values for one or more parameters that define an aspect of the control stimulation pulses delivered by IMD 110 according to that program, such as current or voltage amplitude, pulse width, pulse frequency, electrode combination, and, in some examples timing based on informed stimulation pulses to be delivered to patient 105. In some examples, IMD 110 delivers control stimulation pulses to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from programmer 150 to control delivery of electrical stimulation therapy. For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a clinician programmer if it is primarily intended for use by a clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and programmer 150 may communicate via wireless communication using any techniques known in the art. Examples of communication techniques may include, for example, radiofrequency (RF) telemetry and inductive coupling, but other techniques are also contemplated. In some examples, programmer 150 may include a communication head that may be placed proximate to the patient's body near the IMD 110 implant site to improve the quality or security of communication between IMD 110 and programmer 150. Communication between programmer 150 and IMD 110 may occur during power transmission or separate from power transmission.

In some examples, IMD 110, in response to commands from external programmer 150, delivers electrical stimulation therapy according to a plurality of stimulation programs to a target tissue site of the spinal cord 120 of patient 105 via electrodes (not depicted) on leads 130. In some examples, IMD 110 may modify stimulation programs as therapy needs of patient 105 evolve over time. For example, the modification of the stimulation programs may cause the adjustment of at least one parameter of control stimulation pulses and/or informed stimulation pulses. When patient 105 receives the same therapy for an extended period, the efficacy of the therapy may be reduced. In some cases, parameters of the plurality of control stimulation pulses and/or informed stimulation pulses may be automatically updated.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (e.g., a characteristic of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, control stimulation pulses may also elicit at least one ECAP, and ECAPs responsive to the control stimulation pulses may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters may contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one example, control stimulation pulses and informed stimulation pulses may include one or more informed stimulation pulses and one or more control stimulation pulses. Each informed stimulation pulse may have a pulse width greater than approximately 300 µs, such as between approximately 300 µs and 1000 µs (e.g., 1 millisecond) in some examples. At these pulse widths, IMD 110 may not sufficiently detect an ECAP signal because the informed stimulation pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed stimulation pulses have these longer pulse widths, IMD 110 may deliver control stimulation in the form of control stimulation pulses. The control stimulation pulses may have pulse widths of less than approximately 300 µs, such as a bi-phasic pulse with each phase having a duration of approximately 100 µs. Since the control stimulation pulses may have shorter pulse widths than the informed stimulation pulses, the ECAP signal may be sensed and identified following each control stimulation pulse and used to inform IMD 110 about any changes that should be made to the informed stimulation pulses (and control stimulation pulses in some examples). In general, the term "pulse width" refers to the collective duration of every phase, and interphase interval when appropriate, of a single pulse. A single pulse may include a single phase in some examples (e.g., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 µs, a negative phase lasting 100 µs, and an interphase interval lasting 30 µs defines a pulse width of 230 µs).

As described, the example techniques for adjusting stimulation parameter values for control stimulation pulses and/or informed stimulation pulses are based on comparing the value of a characteristic of a measured ECAP signal to a target ECAP characteristic value. The target ECAP characteristic value is selected from a growth curve that corresponds to a detected posture of the patient because the target ECAP characteristic value that results in a desired efficacy of the stimulation therapy provided to patient 105 may change based on the current posture of patient 105. During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of the patient 105. Examples of the one or more sensors include one or more sensors configured to measure a compound action potential of the patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more therapy parameters that defines the informed stimulation pulses and, in some examples, the control stimulation pulses, delivered to patient 105.

In the example techniques described in this disclosure, the parameters of the control stimulation pulses and the target ECAP characteristic values may be initially set at the clinic but subsequently may be set and/or adjusted at home by patient 105. Once the target ECAP characteristic values are set, the example techniques allow for automatic adjustment of electrical stimulation pulse parameters to maintain consistent volume of neural activation and consistent perception of therapy for patient 105 when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a clinician or patient 105.

In some examples, the system may change the target ECAP characteristic value over a period of time. The system may be programmed to change the target ECAP characteristic in order to adjust the intensity of control stimulation pulses and/or informed stimulation pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 150 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed stimulation pulses and/or control stimulation pulses in order to meet the target ECAP characteristic value.

In some examples, the target ECAP characteristic value may be selected based on an ECAP growth curve for patient 105 that is selected based on a detected posture of patient 105 as described in more detail below. The ECAP growth curve defines a relationship between a parameter defining delivery of electrical stimulation pulses delivered to the patient and a parameter of an ECAP signal of a nerve of a patient elicited by the electrical stimulation pulses. The ECAP growth curve may be determined for patient 105 that is determined based on a slope of a relationship between detected values of a characteristic of ECAP signals for respective different stimulation pulse amplitudes. In some examples, IMD 110 detects a posture of patient 105 and selects a growth curve that corresponds to the detected posture. IMD 110 selects a target ECAP characteristic value from the selected growth curve. IMD 110 determines a difference between the target ECAP characteristic value (e.g., an amplitude value) and a measured ECAP value and multiply the difference by the gain value. IMD 110 uses the resulting value to increase or decrease the previous parameter value that defined the control stimulation pulse that resulted in the measured ECAP value. The gain value can also be used to similarly adjust the parameter values of the informed stimulation pulses. By employing the gain value, IMD 110 may be able to respond quickly to large ECAP signal variations and reset the control stimulation pulses and informed stimulation pulses to the target ECAP. This process may reduce the number of informed stimulation pulses that produce less effective therapy resulting from electrode-to-tissue distance changes during patient movement.

In some examples, the control stimulation pulses may be therapeutic or non-therapeutic. For example, while IMD 110 delivers the control stimulation pulses to elicit an ECAP response of patient 105, the control stimulation pulses may nevertheless provide some therapeutic benefit to patient 105. Typically, one or more control stimulation pulses are at least partially interleaved with one or more informed stimulation pulses.

In accordance with the techniques of the disclosure, IMD 110 selects an ECAP growth curve (or directly selects a target ECAP characteristic value) based on a posture of a patient, the ECAP growth curve for use in controlling the electrical stimulation therapy delivered to the patient. For example, IMD 110 senses a posture of patient 105. IMD 110 selects an ECAP growth curve (or target ECAP characteristic value) based on the sensed posture. IMD 110 may select, based on the selected ECAP growth curve, one or more parameters for defining delivery of control stimulation pulses to patient 105. IMD 110 delivers the control stimulation pulses according to the selected one or more parameters to elicit a detectable ECAP response from a tissue of patient 105. IMD 110 may also sense the ECAP response of patient 105, and select, based on the sensed ECAP response of patient 105, one or more parameters for defining informed stimulation pulses for delivery to patient 105.

IMD 110 delivers the informed stimulation pulses according to the selected one or more parameters to provide therapy to patient 105. For example, in response to determining that a characteristic of the ECAP signal (e.g., a voltage amplitude) has deviated from a target ECAP characteristic value of the ECAP growth curve, IMD 110 may change one or more stimulation parameters of the next one or more informed stimulation pulses to be delivered to the patient. For example, IMD 110 may increase or decrease a current amplitude of the informed stimulation pulses (and the control stimulation pulses, in some examples) by a predetermined step size or based on a gain value representative of the selected growth curve for the patient. In this manner, IMD 110 may use a posture that patient 105 has assumed to select an ECAP growth curve that is appropriate for controlling the adjustment of therapy stimulation delivered to patient 105.

The techniques of the disclosure may enable IMD 110 to maintain a consistent volume of neural activation by adjusting the one or more stimulation parameters of the informed stimulation pulses in proportion to an ECAP growth curve that itself is a function of the sensed posture of the patient. Since the distance between electrodes and target nerves changes with patient posture, selecting an ECAP growth curve specific to the posture at that time may enable IMD 110 to more accurately maintain a consistent volume of neural activation. Therefore, the techniques of the disclosure may enable an IMD to provide electrical stimulation therapy that delivers a consistent level of therapeutic electrical stimulation to the patient, despite changes in the posture of the patient, changes in the position of the leads of the IMD over time, or changes in the biochemistry of the patient. Accordingly, the techniques of the disclosure may provide higher therapeutic efficacy over conventional electrical stimulation systems.

Figure 2A:
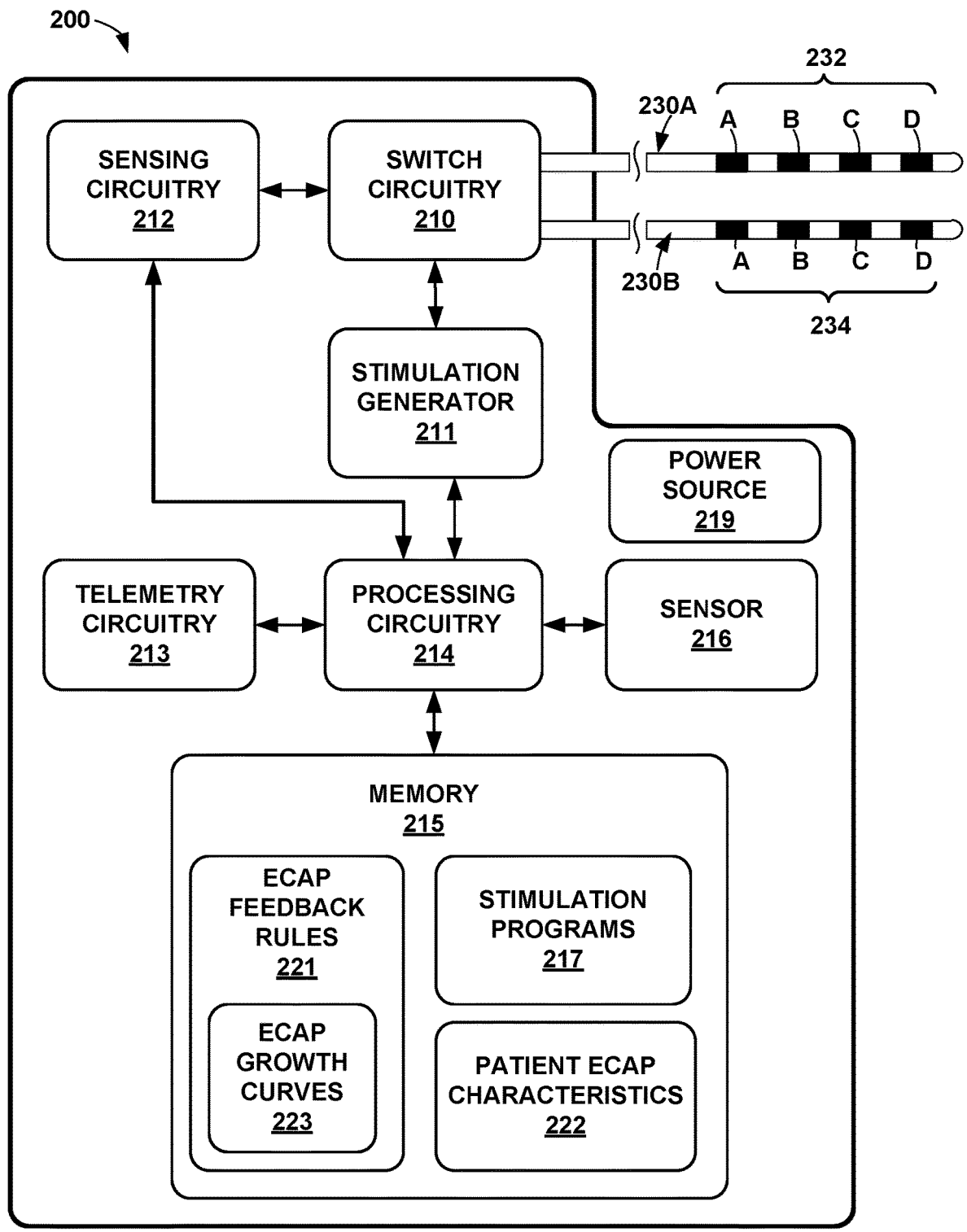
FIG. 2A is a block diagram of the example IMD of FIG. 1.

FIG. 2A is a block diagram of IMD 200. IMD 200 may be an example of IMD 110 of FIG. 1. In the example shown in FIG. 2A, IMD 200 includes processing circuitry 214, memory 215, stimulation generator 211, sensing circuitry 212, telemetry circuitry 213, sensor 216, and power source 219. Each of these circuits may be or include programmable or fixed function circuitry configured to perform the functions attributed to respective circuitry. For example, processing circuitry 214 may include fixed-function or programmable circuitry, stimulation generator 211 may include circuitry configured to generate stimulation signals such as pulses or continuous waveforms on one or more channels, sensing circuitry 212 may include sensing circuitry for sensing signals, and telemetry circuitry 213 may include telemetry circuitry for transmission and reception of signals. Memory 215 may store computer-readable instructions that, when executed by processing circuitry 214, cause IMD 200 to perform various functions. Memory 215 may be a storage device or other non-transitory medium.

In the example shown in FIG. 2A, memory 215 stores stimulation programs 217 that defines values for a set of electrical stimulation parameters (e.g., a stimulation parameter set), such as a stimulation electrode combination, electrode polarity, current or voltage amplitude, pulse width, pulse rate, and pulse shape. In some examples, the pulses defined by one or more stimulation programs 217 may include pulses from which ECAP signals are detectable (e.g., control stimulation pulses). In other examples, stimulation programs 217 may include one or more programs that define stimulation pulses from which ECAP signals are not detectable (e.g., informed stimulation pulses). Therefore, in order to detect ECAP signals for feedback and control as described herein, these programs, or one or more additional programs, may define control stimulation pulses from which ECAP signals are detectable for modulating stimulation parameters that define the informed stimulation pulses. The programs that define informed stimulation programs and control stimulation programs may be stored in the same or separate memories within memory 215.

Memory 215 also stores target ECAP feedback rules 221 and patient ECAP characteristics 222. Each one of stored stimulation programs 217 defines values for a set of electrical stimulation parameters (e.g., a stimulation parameter set), which may define control stimulation pulses and, in some examples, informed stimulation pulses. A single program may define both types of control stimulation pulses and informed stimulation pulses, but in other examples, separate programs within stimulation programs 217 may define the respective informed stimulation pulses and control stimulation pulses for delivery at least partially interleaved with each other. In some examples, the program defining control stimulation pulses may also have additional information such as instructions regarding when to deliver control stimulation pulses based on the pulse width and/or frequency of the informed stimulation pulses defined by the same program, or another program that defines delivery of the informed stimulation pulses.

Accordingly, in some examples, stimulation generator 211 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 210 may include one or more switch arrays, one or more multiplexers, one or more switches (e.g., a switch matrix or other collection of switches), or other electrical circuitry configured to direct stimulation signals from stimulation generator 211 to one or more of electrodes 232, 234, or directed sensed signals from one or more of electrodes 232, 234 to sensing circuitry 212. In other examples, stimulation generator 211 and/or sensing circuitry 212 may include sensing circuitry to direct signals to and/or from one or more of electrodes 232, 234, which may or may not also include switch circuitry 210.

Processing circuitry 214 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 214 herein may be embodied as firmware, hardware, software or any combination thereof. Processing circuitry 214 controls stimulation generator 211 to generate stimulation signals according to stimulation programs 217 stored in memory 215 to apply stimulation parameter values specified by one or more of programs, such as amplitude, pulse width, pulse rate, and pulse shape of each of the stimulation signals.

In the example shown in FIG. 2A, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 214 also controls stimulation generator 211 to generate and apply the stimulation signals to selected combinations of electrodes 232, 234. In some examples, stimulation generator 211 includes a switch circuit (instead of, or in addition to, switch circuitry 210) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2A) with selected electrodes 232, 234.

In other examples, however, stimulation generator 211 does not include a switch circuit and switch circuitry 212 does not interface between stimulation generator 211 and electrodes 232, 234. In these examples, stimulation generator 211 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generator 211, e.g., via switch circuitry 210 and/or switching circuitry of the stimulation generator 211, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 212 is incorporated into a common housing with stimulation generator 211 and processing circuitry 214 in FIG. 2A, in other examples, sensing circuitry 212 may be in a separate housing from IMD 200 and may communicate with processing circuitry 214 via wired or wireless communication techniques.

In some examples, one or more of electrodes 232 and 234 may be suitable for sensing the ECAPs. For instance, electrodes 232 and 234 may sense the voltage amplitude of a portion of the ECAP signals, where the sensed voltage amplitude is a characteristic the ECAP signal.

Sensor 216 may include one or more sensing elements that sense values of a respective patient characteristic, such as posture. As described, electrodes 232 and 234 may be the electrodes that sense the characteristic value of the ECAP. Sensor 216 may include one or more accelerometers, optical sensors, chemical sensors, temperature sensors, pressure sensors, or any other types of sensors. Sensor 216 may output patient characteristic values that may be used as feedback to control delivery of therapy. For example, and as explained in more detail below, sensor 216 may sense a posture of a patient (where posture may include a static posture and/or patient activity), and processing circuitry 214 may adjust one or more parameters of stimulation pulses and ECAP sensing based on the detected posture and/or patient activity. The detected posture of the patient may include one or more of a standing position, an upright position, a sitting position, a prone position, a supine position, a right lateral position, a left lateral position, etc. In one example, processing circuitry 214 may select an ECAP growth curve (or target ECAP characteristic value) for defining stimulation pulses (e.g., control stimulation pulses and/or informed stimulation pulses) and corresponding ECAP sensing based on the detected posture of the patient. IMD 200 may include additional sensors within the housing of IMD 200 and/or coupled via one of leads 130 or other leads. In addition, IMD 200 may receive sensor signals wirelessly from remote sensors via telemetry circuitry 213, for example. In some examples, one or more of these remote sensors may be external to patient (e.g., carried on the external surface of the skin, attached to clothing, or otherwise positioned external to the patient).

Telemetry circuitry 213 supports wireless communication between IMD 200 and an external programmer (not shown in FIG. 2A) or another computing device under the control of processing circuitry 214. Processing circuitry 214 of IMD 200 may receive, as updates to programs, values for various stimulation parameters such as amplitude and electrode combination, from the external programmer via telemetry circuitry 213. Updates to stimulation programs 217 may be stored within memory 215. Telemetry circuitry 213 in IMD 200, as well as telemetry circuits in other devices and systems described herein, such as the external programmer, may accomplish communication by radiofrequency (RF) communication techniques. In addition, telemetry circuitry 213 may communicate with an external medical device programmer (not shown in FIG. 2A) via proximal inductive interaction of IMD 200 with the external programmer. The external programmer may be one example of external programmer 150 of FIG. 1. Accordingly, telemetry circuitry 213 may send information to the external programmer on a continuous basis, at periodic intervals, or upon request from IMD 110 or the external programmer.

Power source 219 delivers operating power to various components of IMD 200. Power source 219 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used.

Stimulation generator 211 of IMD 200 may receive, via telemetry circuitry 213, instructions to deliver electrical stimulation therapy according to stimulation programs 217 to a target tissue site of the spinal cord of the patient via a plurality of electrode combinations of electrodes 232, 234 of leads 230 and/or a housing of IMD 200. Stimulation generator 211 may receive, via telemetry circuitry 213, user instructions to deliver control stimulation pulses to the patient according to stimulation programs 217. Each pulse of a plurality of control stimulation pulses may elicit an ECAP that is sensed by sensing circuitry 212 via some of electrodes 232 and 234. Stimulation programs 217 may instruct stimulation generator 211 to deliver a plurality of control stimulation pulses interleaved with at least some of the plurality of informed stimulation pulses. Processing circuitry 214 may receive, via an electrical signal sensed by sensing circuitry 212, information indicative of an ECAP signal (e.g., a numerical value indicating a characteristic of the ECAP in electrical units such as voltage or power) produced in response to the control stimulation pulses. Stimulation programs 217 may be updated according to the ECAPs recorded at sensing circuitry 212 according to the following techniques.

In one example, the plurality of informed stimulation pulses each have a pulse width of greater than approximately 300 μs and less than approximately 2000 μs (e.g., 2 milliseconds). In some examples, the informed stimulation pulse width is greater than approximately 300 μs and less than approximately 800 μs. In another example, the informed stimulation pulse width is greater than approximately 300 μs and less than approximately 500 μs. In one example, informed stimulation pulses have a pulse width of approximately 450 μs and a pulse frequency of approximately 60 Hertz. Amplitude (current and/or voltage) for the informed stimulation pulses may be between approximately 0.5 mA (or volts) and approximately 10 mA (or volts), although amplitude may be lower or greater in other examples.

Each control stimulation pulse of the plurality of control stimulation pulses may have a pulse width of less than approximately 300 μs. In one example, each control stimulation pulse of the plurality of control stimulation pulses may be a bi-phasic pulse with a positive phase having a width of approximately 100 μs, a negative phase having a width of approximately 100 μs, and an interphase interval having a width of approximately 30 μs. In some examples, the positive phase and negative phase may each be 90 μs or 120 μs in other examples. In other examples, the control stimulation pulses may each have a pulse width of approximately 60 μs or smaller. Due to the relatively long pulse widths of the plurality of informed stimulation pulses, sensing circuitry 212 may be incapable of adequately recording an ECAP signals elicited from an informed stimulation pulse because the informed stimulation pulse itself will occur during the ECAP signal and obscure the ECAP signal. However, stimulation pulses with pulse widths less than approximately 300 microseconds, such as the plurality of control stimulation pulses, may be suited to elicit an ECAP which can be sensed after the control stimulation pulse is completed at sensing circuitry 212 via two or more of electrodes 232 and 234.

Control stimulation pulses delivered for the purpose of eliciting detectable ECAP signals (and providing therapy in some examples) may have a current amplitude between approximately 6 mA and 12 mA in some examples, but higher or lower amplitudes may be used in other examples. The frequency of the control stimulation pulses may be between approximately 50 Hertz and 400 Hertz in some examples, which may match the predetermined pulse frequency of the informed stimulation pulses when one control stimulation pulse is delivered for each informed stimulation pulse. Such a relationship may be present when the control stimulation pulses are fully interleaved (e.g., alternating) with the informed stimulation pulses. However, the frequency of the control stimulation pulses may be delivered at a higher frequency than then informed stimulation pulses when two or more control stimulation pulses are delivered between consecutive informed stimulation pulses. In other examples, the frequency of the control stimulation pulses may be delivered at a lower frequency than the informed stimulation pulses when at least some informed stimulation pulses are delivered without a control stimulation pulse delivered between them. The frequency of the control stimulation pulses may be delivered at a frequency that varies over time if the system is configured to adjust control stimulation pulse delivery, and the resulting ECAP sensing, based on other factors such as patient activity.

In one example, the predetermined pulse frequency of the plurality of informed stimulation pulses may be less than approximately 400 Hertz. In some examples, the predetermined pulse frequency of the plurality of informed stimulation pulses may be between approximately 50 Hertz and 70 Hertz. In one example, the predetermined pulse frequency of the plurality of informed stimulation pulses may be approximately 60 Hertz. However, the informed stimulation pulses may have frequencies greater than 400 Hertz or less than 50 Hertz in other examples. In addition, the informed stimulation pulses may be delivered in bursts of pulses, with interburst frequencies of the pulses being low enough such that a control stimulation pulse and sensed ECAP can still fit within the window between consecutive informed stimulation pulses delivered within the burst of informed stimulation pulses.

Since each informed stimulation pulse of the plurality of informed stimulation pulses may be sensed as an artifact that covers, or obscures, the sensing of at least one ECAP, the plurality of control stimulation pulses may be delivered to the patient during a plurality of time events. For example, a time event (e.g., a window) of the plurality of time events may be a time (e.g., a window) between consecutive informed stimulation pulses of the plurality of informed stimulation pulses at the predetermined pulse frequency. One or more control stimulation pulses of the plurality of control stimulation pulses may be delivered to the patient during each time event. Consequently, the control stimulation pulses may be interleaved with at least some of the informed stimulation pulses such that the plurality of control stimulation pulses are delivered to the patient while informed stimulation pulses are not delivered. In one example, an ECAP elicited from to a control stimulation pulse delivered during a time event may be recorded by sensing circuitry 212 during the same time event. In another example, two or more ECAPs responsive to two or more respective control stimulation pulses delivered during a time event may be recorded by sensing circuitry 212 during the same time event.

In some examples, stimulation programs 217 may be updated according to a plurality of ECAPs received in response to the plurality of control stimulation pulses delivered to the patient. For instance, processing circuitry 214 may update stimulation programs 217 (or merely update parameter values defining control stimulation pulses and/or informed stimulation pulses) in real time by comparing one or more characteristics of ECAPs sensed by sensing circuitry 212 with target ECAP characteristics stored in memory 215 (e.g., patient ECAP characteristics 222). For example, processing circuitry 214 is configured to determine a characteristic value (e.g., an amplitude) of each ECAP signal received at sensing circuitry 212, and processing circuitry 214 is further configured to determine the representative characteristic value of at least one respective ECAP signal and compare the representative characteristic value of a series of ECAP signals to a target ECAP adjustment window (e.g., the target ECAP characteristic value plus and minus a variance which is stored in patient ECAP characteristics 222). Target ECAP adjustment window may thus be a range of characteristic values deviating from target ECAP characteristic value. For instance, the target ECAP adjustment window may span from a lower-bound characteristic value (e.g., the target ECAP characteristic value minus the variance) to an upper-bound characteristic value (e.g., the target ECAP characteristic value plus the variance). Generally, the lower-bound characteristic value is less than the target ECAP characteristic value, and the upper-bound characteristic value is greater than target ECAP characteristic value.

If the representative characteristic value of the at least one respective ECAP signal (e.g., a characteristic value of a single ECAP signal or an average of two or more ECAP characteristic values) is greater than the upper-bound characteristic value, processing circuitry 214 may adjust one or more parameters defining of informed stimulation pulses and/or control stimulation pulses to decrease the amplitude of informed stimulation pulses and control stimulation pulses, respectively, following the at least one respective ECAP. The amplitude of informed stimulation pulses and control stimulation pulses may be decreased by different predetermined steps or different predetermined percentages. Additionally, if the representative characteristic value of the at least one respective ECAP is less than the lower-bound characteristic value, processing circuitry 214 may adjust parameters defining informed stimulation pulses and/or control stimulation pulses, and the programs 217 may instruct stimulation generator 211 to increase the amplitude of informed stimulation pulses and/or control stimulation pulses following the at least one respective ECAP. Moreover, if the representative characteristic value of the at least one respective ECAP is greater than the lower-bound characteristic value and less than the upper-bound characteristic value, processing circuitry 214 may not change programs 217, and stimulation generator 211 may maintain the amplitude of the informed stimulation pulses following the at least one respective ECAP. In one example, adjusting the programs 217 may include changing one or more parameters of the plurality of informed stimulation pulses and the plurality of control stimulation pulses. In one example, the at least one respective ECAP may include a series of four consecutive ECAPs.

Processing circuitry 214, in one example, may change the amplitude of the informed stimulation pulses and the control stimulation pulses following the at least one respective ECAP inversely proportional to the difference between the target ECAP characteristic value and the representative characteristic value of the at least one respective ECAP. For instance, if the representative characteristic value of the at least one respective ECAP is 20% lower than the target ECAP characteristic value, then processing circuitry 214 may update stimulation programs 217 such that the amplitude of informed stimulation pulses and the control stimulation pulses is increased by 20%. In one example, the representative characteristic value may be the mean characteristic value of two or more respective ECAP signals sensed by sensing circuitry 212. In other examples, the representative characteristic value may be the median characteristic value of two or more respective ECAP signals, or a rolling average of the characteristic values of two or more respective ECAP signals.

In another example, processing circuitry 214 may determine the characteristic value of a respective ECAP signal sensed by sensing circuitry 212. In response to a comparison between the characteristic value of the respective ECAP signal and the target ECAP characteristic value stored in patient ECAP characteristics 222, processing circuitry 214 may determine a percentage difference between the characteristic value of the respective ECAP signal and target ECAP characteristic value. Consequently, processing circuitry 214 may adjust the amplitude of subsequent informed stimulation pulses to be inversely proportional to the percentage difference between the characteristic value of the respective ECAP and target ECAP characteristic value.

In other examples, processing circuitry 214 may use the representative amplitude of the at least one respective ECAP to change other parameters of informed stimulation pulses to be delivered, such as pulse width, pulse frequency, and pulse shape. All of these parameters may contribute to the intensity of the informed stimulation pulses, and changing one or more of these parameter values may effectively adjust the informed stimulation pulse intensity to compensate for the changed distance between the stimulation electrodes and the nerves indicated by the representative amplitude of the ECAP signals.

In some examples, leads 230 may be linear 8-electrode leads (not pictured); sensing and stimulation delivery may each be performed using a different set of electrodes. In a linear 8-electrode lead, each electrode may be numbered consecutively from 0 through 7. For instance, a control stimulation pulse may be generated using electrode 1 as a cathode and electrodes 0 and 2 as anodes (e.g., a guarded cathode), and a respective ECAP signal may be sensed using electrodes 6 and 7, which are located on the opposite end of the electrode array. This strategy may minimize the interference of the stimulation pulse with the sensing of the respective ECAP. Other electrode combinations may be implemented, and the electrode combinations may be changed using the patient programmer via telemetry circuitry 213. For example, stimulation electrodes and sensing electrodes may be positioned closer together. Shorter pulse widths for the control stimulation pulses may allow the sensing electrodes to be closer to the stimulation electrodes.

ECAP feedback rules 221 may define how processing circuitry 214 uses the sensed ECAP signals as feedback for changing one or more stimulation parameters that define respective control stimulation pulses and/or informed stimulation pulses and stored as stimulation programs 217. For example, ECAP feedback rules 221 may specify that the percentage difference between the representative ECAP characteristic value and the target ECAP characteristic value is used to inversely adjust the current amplitude of informed stimulation pulses to the same proportion as the percentage difference. As another example, ECAP feedback rules 221 may specify that the difference between the target ECAP characteristic value is multiplied by a gain value and added to the previous current amplitude of the informed stimulation pulses and control stimulation pulses. In any case, ECAP feedback rules 221 may instruct processing circuitry 14 how to adjust informed stimulation pulses and/or control stimulation pulses based on the sensed ECAP signals.

In accordance with the techniques of the disclosure, ECAP feedback rules 221 further define a plurality of ECAP growth curves 223. Each ECAP growth curve 223 is associated with one or more particular postures of the patient and is based on a slope of the relationship between detected values of a characteristic of ECAP signals for respective different stimulation pulse amplitudes while the patient has assumed the corresponding posture. Processing circuitry 214 may use a sensed current posture of the patient to select an ECAP growth curve from ECAP feedback rules 221 that corresponds to the current posture of the patient for use in defining how processing circuitry 214 uses the sensed ECAP signals as feedback for changing one or more informed stimulation pulse parameters that define informed stimulation pulses.

In one example, sensor 216 may detect a change in activity or a change in posture of the patient. Processing circuitry 214 may receive an indication from sensor 216 that the activity level or posture of the patient is changed, which may indicate that the distance between electrodes and nerves has likely changed. Processing circuitry 214 retrieves one or more ECAP feedback rules, including one of ECAP growth curves 223, that correspond to the new posture of the patient. Processing circuitry 214 selects, based on the selected ECAP growth curve 223, one or more parameters for defining delivery of control stimulation pulses to the patient. Processing circuitry 214 controls stimulation generator 211 to deliver the control stimulation pulses according to the one or more parameters to the patient to elicit detectable ECAP response from a tissue of the patient.

Processing circuitry 214 may use the representative amplitude of a detected ECAP response to select one or more parameters of one or more informed stimulation pulses to be delivered to the patient, such as pulse amplitude, pulse width, pulse frequency, or pulse shape. Processing circuitry 214 controls stimulation generator 211 to deliver the informed stimulation pulses according the selected one or more parameters to provide therapy to the patient. For example, in response to determining that a characteristic of the ECAP signal (e.g., a voltage amplitude) has deviated from a target ECAP characteristic of the ECAP growth curve, processing circuitry 214 may change one or more stimulation parameters of the next one or more informed stimulation pulses to be delivered to the patient. For example, processing circuitry 214 may increase or decrease a current amplitude of the informed stimulation pulses by a predetermined step size or based on a gain value representative of the selected ECAP growth curve for the patient. In this manner, processing circuitry 214 may use a posture that the patient has assumed to select an ECAP growth curve for controlling the adjustment of control stimulation pulses delivered to the patient, thereby adjusting the ECAP feedback rules for controlling the delivery of informed stimulation pulses to the patient.

The techniques of the disclosure may enable IMD 200 to maintain a consistent volume of neural activation by adjusting the one or more stimulation parameters defining the control stimulation pulses and/or informed stimulation pulses in proportion to an ECAP growth curve that itself is a function of the posture of the patient. Therefore, the techniques of the disclosure may enable an IMD to provide electrical stimulation therapy that delivers a consistent level of therapeutic electrical stimulation to the patient, despite changes in the posture of the patient, changes in the position of the leads of the IMD over time, or changes in the biochemistry of the patient. Accordingly, the techniques of the disclosure may provide higher therapeutic efficacy over conventional electrical stimulation systems.

Figure 2B:
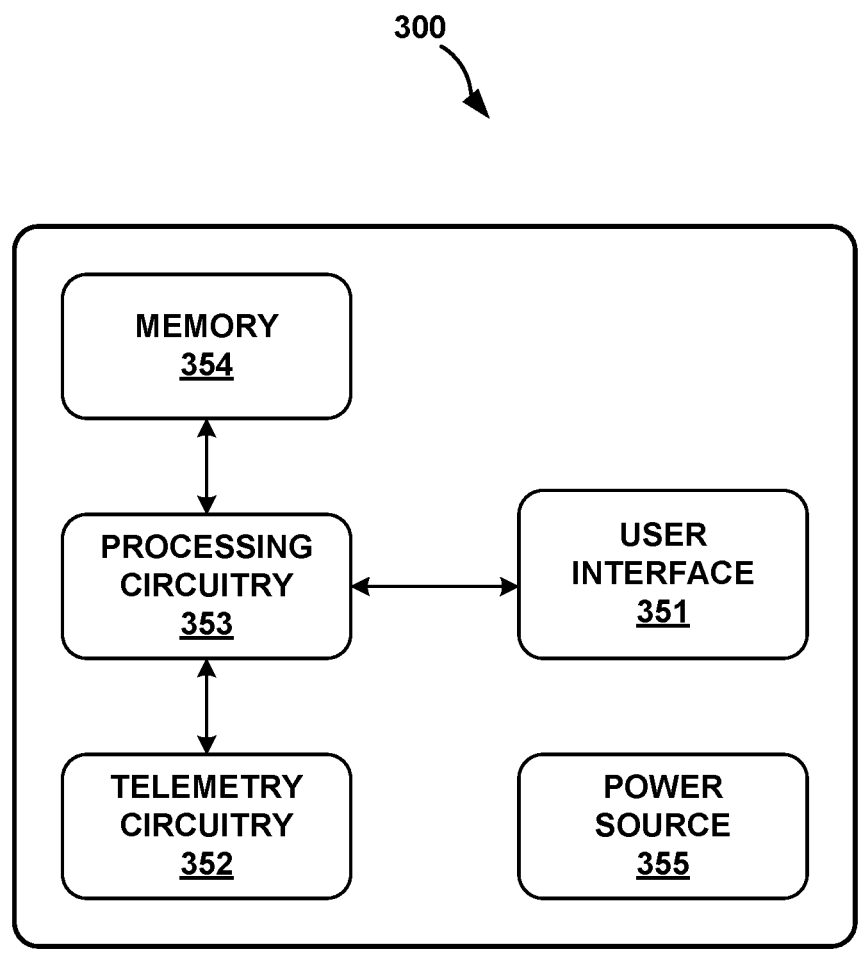
FIG. 2B is a block diagram of the example external programmer of FIG. 1.

FIG. 2B is a block diagram of the example external programmer 300. External programmer 300 may be an example of external programmer 150 of FIG. 1. Although programmer 300 may generally be described as a hand-held device, programmer 300 may be a larger portable device or a more stationary device. In addition, in other examples, programmer 300 may be included as part of an external charging device or include the functionality of an external charging device. As illustrated in FIG. 2B, programmer 300 may include a processing circuitry 353, memory 354, user interface 351, telemetry circuitry 352, and power source 355. Memory 354 may store instructions that, when executed by processing circuitry 353, cause processing circuitry 353 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 353 may include processing circuitry configured to perform the processes discussed with respect to processing circuitry 353.

In general, programmer 300 comprises any suitable arrangement of hardware, alone or in combination with software and/or firmware, to perform the techniques attributed to programmer 300, and processing circuitry 353, user interface 351, and telemetry circuitry 352 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 354, such as RAM, ROM, PROM, EPROM, EEPROM, flash memory, a hard disk, a CD-ROM, comprising executable instructions for causing the one or more processors to perform the actions attributed to them. Moreover, although processing circuitry 353 and telemetry circuitry 352 are described as separate modules, in some examples, processing circuitry 353 and telemetry circuitry 352 are functionally integrated. In some examples, processing circuitry 353 and telemetry circuitry 352 correspond to individual hardware units, such as ASICs, DSPs, FPGAs, or other hardware units.

Memory 354 (e.g., a storage device) may store instructions that, when executed by processing circuitry 353, cause processing circuitry 353 and programmer 300 to provide the functionality ascribed to programmer 300 throughout this disclosure. For example, memory 354 may include instructions that cause processing circuitry 353 to obtain a parameter set from memory, select a spatial electrode movement pattern, or receive a user input and send a corresponding command to IMD 300, or instructions for any other functionality. In addition, memory 354 may include a plurality of programs, where each program includes a parameter set that defines stimulation pulses that may include control stimulation pulses and, in some examples, informed stimulation pulses. Memory 354 may also store data received from a medical device (e.g., IMD 110). For example, memory 354 may store ECAP related data recorded at a sensing module of the medical device, and memory 354 may also store data from one or more sensors of the medical device.

User interface 351 may include a button or keypad, lights, a speaker for voice commands, a display, such as a liquid crystal (LCD), light-emitting diode (LED), or organic light-emitting diode (OLED). In some examples the display may be a touch screen. User interface 351 may be configured to display any information related to the delivery of electrical stimulation, identified patient behaviors, sensed patient characteristic values, patient behavior criteria, or any other such information. User interface 351 may also receive user input via user interface 351. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 352 may support wireless communication between the medical device and programmer 300 under the control of processing circuitry 353. Telemetry circuitry 352 may also be configured to communicate with another computing device via wireless communication techniques, or direct communication through a wired connection. In some examples, telemetry circuitry 352 provides wireless communication via an RF or proximal inductive medium. In some examples, telemetry circuitry 352 includes an antenna, which may take on a variety of forms, such as an internal or external antenna.

Examples of local wireless communication techniques that may be employed to facilitate communication between programmer 300 and IMD 110 include RF communication according to the 802.11 or Bluetooth specification sets or other standard or proprietary telemetry protocols. In this manner, other external devices may be capable of communicating with programmer 300 without needing to establish a secure wireless connection. As described herein, telemetry circuitry 352 may be configured to transmit a spatial electrode movement pattern or other stimulation parameter values to IMD 110 for delivery of electrical stimulation therapy.

In some examples, selection of therapy parameters or therapy stimulation programs may be transmitted to the medical device for delivery to the patient. In other examples, the therapy may include medication, activities, or other instructions that the patient must perform themselves or a caregiver perform for the patient. In some examples, programmer 300 may provide visual, audible, and/or tactile notifications that indicate there are new instructions. Programmer 300 may require receiving user input acknowledging that the instructions have been completed in some examples.

Figure 3:
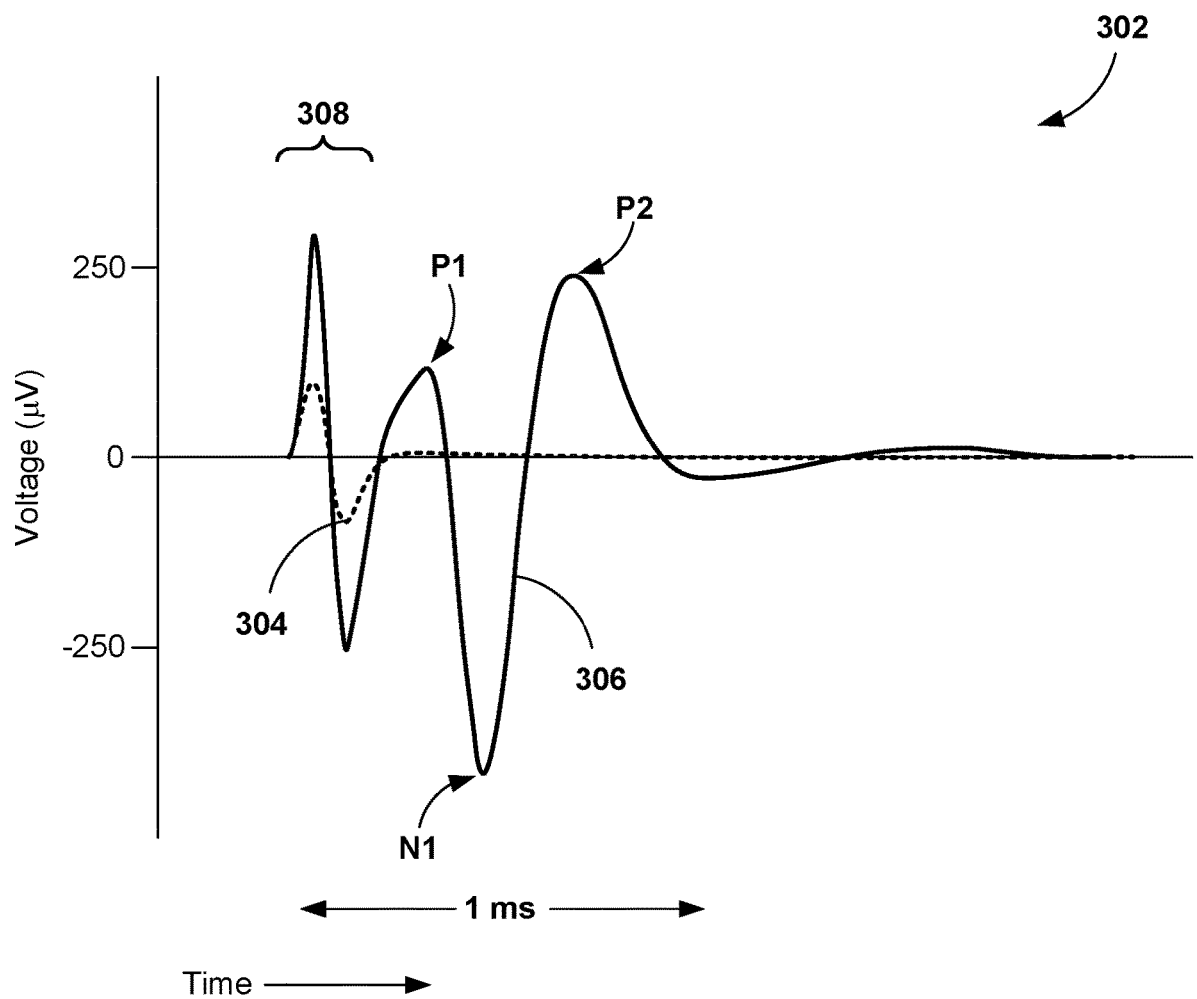
FIG. 3 is a graph of example evoked compound action potentials (ECAPs) sensed for respective stimulation pulses.

FIG. 3 is a graph 302 of example evoked compound action potentials (ECAPs) sensed for respective stimulation pulses. As shown in FIG. 3, graph 302 shows example ECAP signal 304 (dotted line) and ECAP signal 306 (solid line). Each of ECAP signals 304 and 306 may be sensed from respective control stimulation pulses that were delivered from a guarded cathode and bi-phasic pulses including an interphase interval between each positive and negative phase of the pulse. The guarded cathode of the stimulation electrodes may be located at the end of an 8-electrode lead while two sensing electrodes are provided at the other end of the 8-electrode lead. ECAP signal 304 illustrates the voltage amplitude sensed as a result from a sub-threshold stimulation pulse (e.g., a stimulation pulse that does not elicit an ECAP signal because the pulse was below the threshold to cause nerve depolarization). Peaks 308 of ECAP signal 304 are detected and represent the artifact of the delivered control stimulation pulse. However, no propagating signal is detected after the artifact in ECAP signal 304 because the control stimulation pulse was sub-threshold.

In contrast to ECAP signal 304, ECAP signal 306 represents the voltage amplitude detected from a supra-threshold control stimulation pulse. Peaks 308 of ECAP signal 306 are detected and represent the artifact of the delivered control stimulation pulse. After peaks 308, ECAP signal 306 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 306, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control subsequent stimulation pulses (e.g., control stimulation pulses and/or informed stimulation pulses) may be an amplitude of P1, N1, or P2 with respect to neutral or zero voltage. In some examples, the characteristic of the ECAP used to control subsequent stimulation pulses may be a sum of two or more of peaks P1, N1, or P2. In other examples, the characteristic of ECAP signal 306 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between when the stimulation pulse is delivered and a point in the ECAP signal may be referred to as a latency of the ECAP and may indicate the types of fibers being captured by the control stimulation pulse. ECAP signals with lower latency (e.g., smaller latency values) indicate a higher percentage of nerve fibers that have faster propagation of signals, whereas ECAP signals with higher latency (e.g., larger latency values) indicate a higher percentage of nerve fibers that have slower propagation of signals. Other characteristics of the ECAP signal may be used in other examples.

The amplitude of the ECAP signal increases with increased amplitude of the control stimulation pulse, as long as the pulse amplitude is greater than threshold such that nerves depolarize and propagate the signal. The target ECAP characteristic (e.g., the target ECAP amplitude) may be determined from the ECAP signal detected from a control stimulation pulse when informed stimulation pulses are determined to deliver effective therapy to the patient. The ECAP signal thus is representative of the distance between the stimulation electrodes and the nerves appropriate for the stimulation parameter values of the informed stimulation pulses delivered at that time. Therefore, IMD 110 may attempt to use detected changes to the measured ECAP characteristic value to change informed stimulation pulse parameter values and maintain the target ECAP characteristic value during informed stimulation pulse delivery.

Figure 4A:
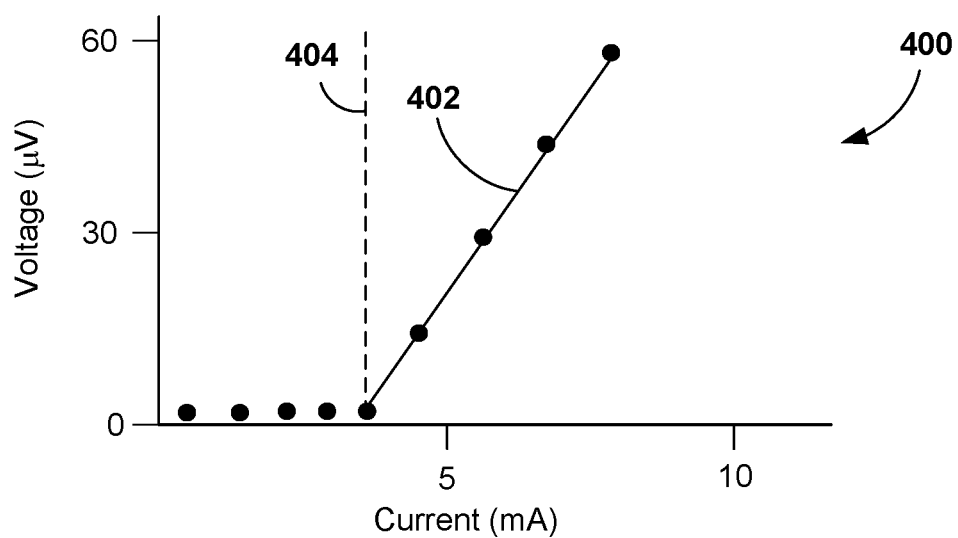
FIG. 4A is a graph of an example growth curve of sensed ECAPs from respective stimulation pulse amplitudes.

FIG. 4A is a graph 400 of an example growth curve 402 derived from sensed ECAPs from respective stimulation pulse amplitudes. For convenience, graph 400 is described with reference to FIG. 1. Graph 400 illustrates example characteristic values of ECAP signals shown as dots for respective different current amplitudes of stimulation pulses. Typically, ECAPs will not be generated until the stimulation pulse amplitude reaches a stimulation threshold 404, approximately at 4.5 mA current in the example of FIG. 4A.

After the current amplitude exceeds stimulation threshold 404, the ECAP characteristic value may increase approximately linearly as the current amplitude is further increased. This linear relationship is shown by growth curve 402. In the example of FIG. 4A, this slope may be approximately 32 µV/mA. However, the slope may vary (e.g., larger or smaller) for each patient based on the type of electrodes implanted, where the electrodes are implanted, the sensitivity of the patient's neurons to stimulation, neurological dysfunction, or other factors.

Furthermore, the techniques of the disclosure recognize that the slope of growth curve 402 can also change depending on a posture of the patient. This is because as the patient changes posture, different positions of the body of the patient (e.g., standing, sitting, laying down) may cause the electrodes disposed along leads 130 of IMD 110 to move slightly closer to or farther from the nerves of the target tissue of patient 105. Thus, as the posture of patient 105 changes, the volume of neural activation may change even though the parameters of the control stimulation pulses delivered to elicit an ECAP response, or parameters of the informed stimulation pulses delivered to provide therapy to patient 105 do not change.

The slope of this growth curve that linearly increases may be referenced as the "gain" herein, as it indicates the relationship between sensed ECAP characteristic values and pulse amplitudes. Put another way, the gain value may represent the slope of the growth curve of values of the characteristic of ECAP signals (e.g., an amplitude such as the N1-P2 amplitude or the amplitude of any peak of the ECAP signal) elicited from respective calibration stimulation pulses delivered to the patient and at least partially defined by different values of a stimulation parameter (e.g., current amplitude, voltage amplitude, or pulse width). For example, the gain value for a patient may be used to dynamically adjust control stimulation pulse amplitude and/or informed stimulation pulse amplitude based on the sensed ECAP characteristic values. In some examples, the gain may be approximated for a patient based on historical data for similar patients. In other examples, the system may generate a custom growth curve and gain specific to the patient before starting therapy with the system.

Figure 4B:
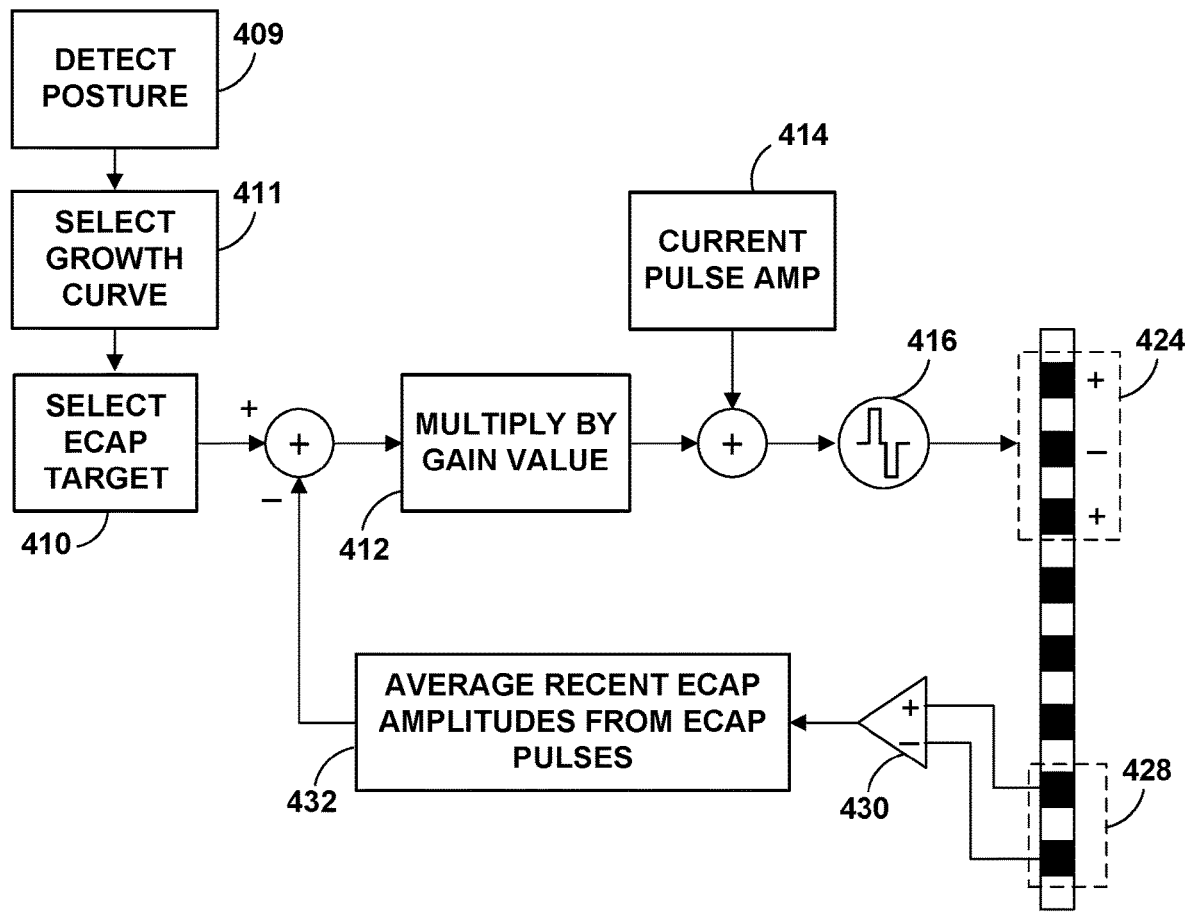
FIG. 4B is a diagram illustrating an example technique for adjusting stimulation therapy.

FIG. 4B is a diagram illustrating an example technique for adjusting stimulation therapy. As shown in the example of FIG. 4B, the system, such as IMD 200 or any other device or system described herein, may dynamically adjust an amplitude (or other parameter) of electrical stimulation pulses based on the gain value representing the patient sensitivity to stimulation. As described above, processing circuitry 214 of IMD 200 selects a gain value of an ECAP growth curve that is associated with a current posture of the patient. Processing circuitry 214 controls stimulation generator 211 to deliver a stimulation pulse to a patient. Processing circuitry 214 may then control sensing circuitry 212 to sense an ECAP signal elicited by the stimulation pulse and then identify a characteristic of the ECAP signal (e.g., an amplitude of the ECAP signal). In the example of FIG. 4B, the characteristic value of the ECAP signal is an amplitude. However, in other examples, the characteristic value of the ECAP signal may take other forms, such as a sum of two or more peaks in the ECAP signal, an area under one or more peaks in the ECAP signal, a time between two points in the ECAP signal, a slope between two points in the ECAP signal, a latency of the ECAP signal, or other types of ECAP characteristics described herein. Processing circuitry 214 may then determine, based on the characteristic of the ECAP signal and a gain value, a stimulation parameter value (e.g., an amplitude, pulse width value, pulse frequency value, and/or slew rate value) that at least partially defines a subsequent stimulation pulse. Processing circuitry 214 may then control stimulation generator 211 to deliver the subsequent stimulation pulse according to the determined stimulation parameter value.

As shown in FIG. 4B, a stimulation pulse 416 (e.g., a control stimulation pulse from which an ECAP is detectable) is delivered to the patient via electrode combination 424. The resulting ECAP is sensed by the two electrodes at the opposing end of the lead of electrode combination 428 fed to a differential amplifier 430. For each sensed ECAP, processing circuitry 214 may measure an amplitude of a portion of the ECAP signal, such as the N1-P2 voltage amplitude from the portion of the ECAP signal. Processing circuitry 214 may average 432 the recently measured ECAP amplitudes, such as averaging the most recent, and consecutive, 2, 3, 5, 5, 6, or more ECAP amplitudes. In some examples, the average 432 may be a mean or median value. In other examples, average 432 may be a weighted average of recent ECAP amplitudes that weights recent amplitudes higher than older amplitudes. In some examples, one or more ECAP amplitudes may be ignored from the calculations if the amplitude value is determined to be an error.

Processing circuitry 214 may also detect a posture 409 of patient 105 at a predetermined frequency and/or on demand. Processing circuitry 214 selects an ECAP growth curve 411 associated with the detected posture 409 of the patient. Processing circuitry 214 may then select a target ECAP amplitude 410 from the selected ECAP growth curve 411. In some examples, the target ECAP amplitude 410 is greater than a perception threshold of the patient along the selected ECAP growth curve 411. In some examples, the target ECAP amplitude 410 is less than a discomfort threshold of the patient along the selected ECAP growth curve 411. In some examples, the target ECAP amplitude 410 is a midpoint on the selected ECAP growth curve 411 that is between the perception threshold and discomfort threshold. Each of the perception threshold and discomfort threshold may be determined by a clinician during initial calibration of IMD 200. This target ECAP amplitude 410 may essentially represent a reference distance between the stimulation electrodes and the target neurons (e.g., the spinal cord for the case of SCS) when patient 105 is in the posture corresponding to the selected ECAP growth curve 411.

The measured amplitude (or average measured amplitude) 432 is then subtracted from the selected target ECAP amplitude 410 to generate a differential amplitude. The differential amplitude is then multiplied by the gain value for the patient to generate a preliminary differential value 412. The differential value is then added to the previously delivered pulse amplitude 414 (e.g., the currently stored amplitude value) to generate the new, or adjusted, pulse amplitude that at least partially defines the next stimulation pulse 416. The next stimulation pulse 416 is then delivered to the patient via electrode combination 424. Although electrode combination 424 is different than electrode combination 428, electrode combination 424 can be any set of electrodes on the lead as desired for therapy because the stimulation pulse is delivered in a non-overlapping fashion with sensed ECAP signals.

In some examples, the stimulation pulse width may be less than approximately 300 µs. In some examples, the stimulation pulse is a bi-phasic pulse including a positive phase and a negative phase. For example, a bi-phasic stimulation pulse may include a positive phase having a duration of approximately 100 µs, a negative phase having a duration of approximately 100 µs, and an interphase interval of an approximately 30 µs duration. In this manner, the stimulation pulse may be completed prior to detection of the resulting ECAP signal. In some examples, one or more parameters of the stimulation pulse are selected so as not to interfere with the sensing of the resulting ECAP signal or the production of a detectable ECAP signal.

Although the technique of FIG. 4B is described for adjusting the amplitude of the stimulation pulses, other parameter values may be changed in other examples. For example, sensed ECAP signals may be used to increase or decrease the pulse width of the stimulation pulse to adjust the amount of charge delivered to the tissue to maintain consistent volume of neural activation. In other examples, electrode combinations may be adjusted in order to deliver different amounts of charge and modify the number of neurons being recruited by each stimulation pulse. In other examples, processing circuitry 214 may be configured to adjust the slew rate of the stimulation pulses (e.g., the rate of change of the voltage and/or amplitude at the beginning and/or end of the pulse or each phase of the pulse) in response to a characteristic of the ECAP signal, such as the amplitude of recent ECAP amplitudes. For parameters other than amplitude, gain values may need to be determined that are specific for each type of parameter in order to appropriately adjust that type of parameter. Processing circuitry 214 may change one or more parameters defining the stimulation pulse according to the process described here with respect to FIG. 4B. For example, the ECAP signal may be used to control multiple concurrent feedback mechanisms simultaneously for respective pulse parameters. In other examples, processing circuitry 214 may switch between two or more feedback mechanisms when processing circuitry 214 reaches a limit of adjustment for a specific parameter. For example, processing circuitry 214 may be configured to use a feedback control mechanism to adjust amplitude as long as the amplitude remains within a range (e.g., a range defined by the clinician) and then switch to a different feedback control mechanism to adjust a different parameter (e.g., pulse width or slew rate) of the stimulation pulses in response to the amplitude exceeding the range.

Figure 4C:
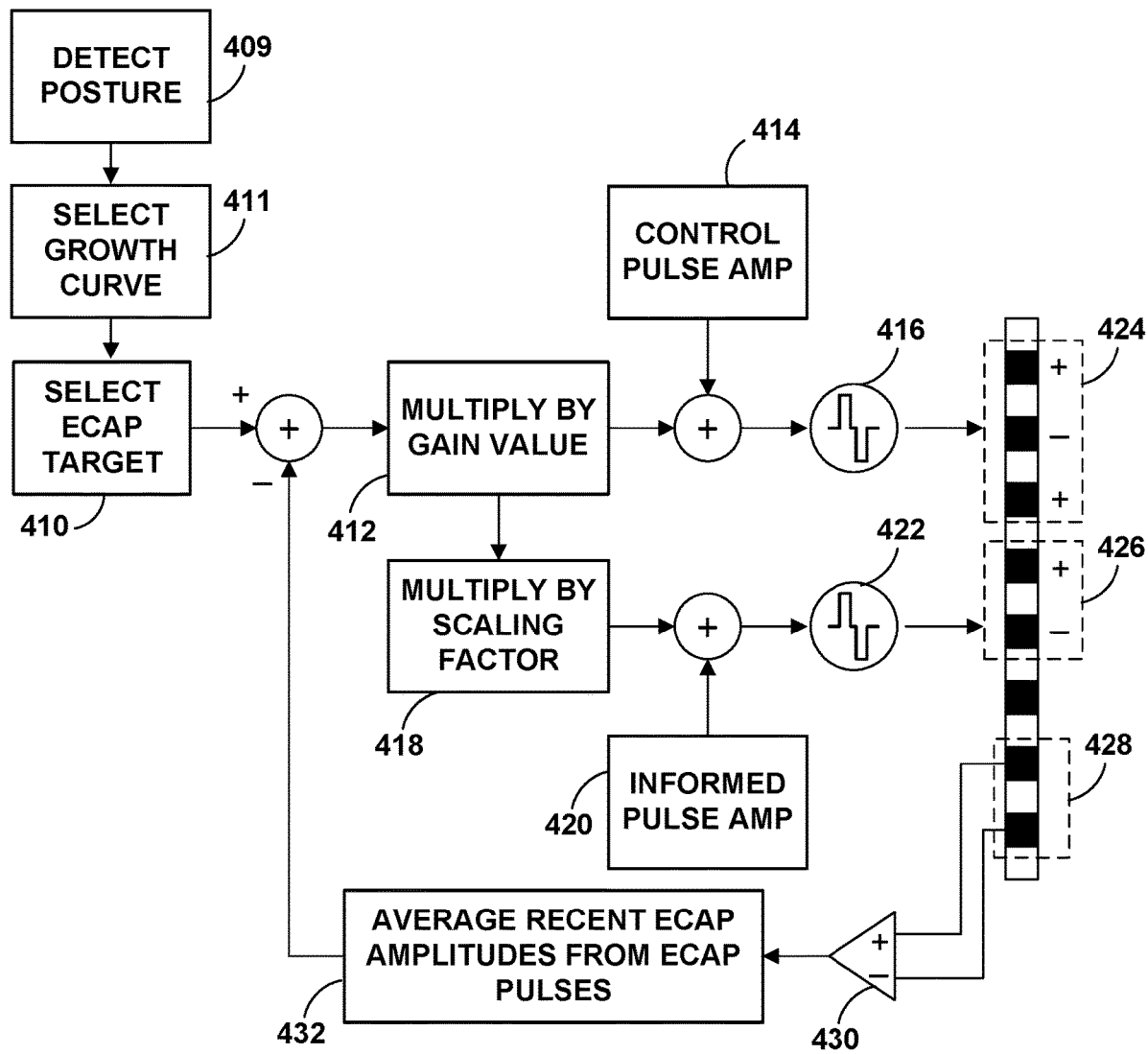
FIG. 4C is a diagram illustrating an example technique for adjusting stimulation therapy.

FIG. 4C is a diagram illustrating an example technique for adjusting stimulation therapy. As shown in the example of FIG. 4C, the system, such as IMD 200 or any other device or system described herein, may dynamically adjust an amplitude (or other parameter) of informed stimulation pulses and control stimulation pulses based on the gain value representing the patient sensitivity to stimulation. As described above, processing circuitry 214 of IMD 200 selects a gain value of an ECAP growth curve that is associated with a current posture of the patient. Processing circuitry 214 controls stimulation generator 211 to deliver a control stimulation pulse to a patient. Processing circuitry 214 may then control sensing circuitry 212 to sense an ECAP signal elicited by the control stimulation pulse and then identify a characteristic of the ECAP signal (e.g., an amplitude of the ECAP signal). In the example of FIG. 4C, the characteristic value of the ECAP signal is an amplitude. However, in other examples, the characteristic value of the ECAP signal may take other forms, such as a sum of two or more peaks in the ECAP signal, an area under one or more peaks in the ECAP signal, a time between two points in the ECAP signal, a slope between two points in the ECAP signal, a latency of the ECAP signal, or other types of ECAP characteristics described herein. Processing circuitry 214 may then determine, based on the characteristic of the ECAP signal and a gain value, an informed stimulation parameter value (e.g., an amplitude, pulse width value, pulse frequency value, and/or slew rate value) that at least partially defines an informed stimulation pulse. Processing circuitry 214 may then control stimulation generator 211 to deliver the informed stimulation pulse according to the determined informed stimulation parameter value.

As shown in FIG. 4C, a control stimulation pulse 416 is delivered to the patient via electrode combination 424, shown as a guarded cathode of three electrodes. The resulting ECAP is sensed by the two electrodes at the opposing end of the lead of electrode combination 428 fed to a differential amplifier 430. For each sensed ECAP, processing circuitry 214 may measure an amplitude of a portion of the ECAP signal, such as the N1-P2 voltage amplitude from the portion of the ECAP signal. Processing circuitry 214 may average 432 the recently measured ECAP amplitudes, such as averaging the most recent, and consecutive, 2, 3, 5, 5, 6, or more ECAP amplitudes. In some examples, the average 432 may be a mean or median value. In some examples, one or more ECAP amplitudes may be ignored from the calculations if the amplitude value is determined to be an error.

Processing circuitry 214 detects a posture 409 of patient 105. Processing circuitry 214 selects an ECAP growth curve 411 associated with posture 409 of patient 411. Processing circuitry 214 selects a target ECAP amplitude along the selected ECAP growth curve 411. In some examples, the target ECAP amplitude is greater than a perception threshold of the patient along the selected ECAP growth curve 411. In some examples, the target ECAP amplitude is less than a discomfort threshold of the patient along the selected ECAP growth curve 411. In some examples, the target ECAP amplitude is a midpoint on the selected ECAP growth curve 411 that is between the perception threshold and discomfort threshold. Each of the perception threshold and discomfort threshold may be determined by a clinician during initial calibration of IMD 200. This target ECAP amplitude 410 may essentially represent a reference distance between the stimulation electrodes and the target neurons (e.g., the spinal cord for the case of SCS) when patient 105 is in the posture corresponding to the selected ECAP growth curve 411.

The measured amplitude (or average measured amplitude) 432 is then subtracted from the selected target ECAP amplitude 410 to generate a differential amplitude. The differential amplitude is then multiplied by the gain value for the patient to generate a preliminary differential value 412. The preliminary differential value is added to the ECAP pulse amplitude (e.g., the non-therapeutic pulse amplitude) to generate the new, or adjusted, ECAP pulse amplitude that at least partially defines the next informed stimulation pulse 416.

To adjust the informed stimulation pulse amplitude, the differential value is multiplied by a scaling factor 418 to generate the informed differential value. The scaling factor 418 may be implemented because the ECAP signal is sensed from the control stimulation pulse which may be different from the informed stimulation pulse. For example, the scaling factor may the ratio of the previously delivered informed stimulation pulse amplitude to the previously delivered control stimulation pulse amplitude. The informed differential value is then added to the previously delivered informed stimulation pulse amplitude to generate the new, or adjusted, informed stimulation pulse amplitude that at least partially defines the next informed stimulation pulse 422. The next informed stimulation pulse 422 is then delivered, interleaved with control stimulation pulse 416, to the patient via electrode combination 426. In some examples, at least two control stimulation pulses may be delivered, and at least two respective ECAP signals sensed, between consecutive informed stimulation pulses. This increased frequency of control stimulation pulses may allow the system to quickly adjust informed stimulation pulse amplitudes for any changes in the distance between electrodes and neurons. Although electrode combination 426 is different than electrode combinations 424 and 428, electrode combination 426 can be any set of electrodes on the lead as desired for therapy because the informed stimulation pulse is delivered in a non-overlapping fashion with control stimulation pulses and sensed ECAP signals.

In some examples, the pulse width of the informed stimulation pulse may be greater than approximately 300 µs and less than approximately 1000 µs. In other examples, the pulse width of the informed stimulation pulse may be less than approximately 300 µs or greater than 1000 µs. The informed stimulation pulse may be a monophasic pulse followed a passive recharge phase. However, in other examples, the informed stimulation pulse may be a bi-phasic pulse that includes a positive phase and a negative phase. In some examples, the control stimulation pulse width may be less than approximately 300 µs. In some examples, the control stimulation pulse is a bi-phasic pulse including a positive phase and a negative phase. For example, a bi-phasic control stimulation pulse may include a positive phase having a duration of approximately 100 µs, a negative phase having a duration of approximately 100 µs, and an interphase interval of an approximately 30 µs duration. In this manner, the control stimulation pulse may be completed prior to detection of the resulting ECAP signal. In some examples, an informed stimulation pulse may be less than 300 µs, but the following passive recharge phase or even an active recharge phase (of a bi-phasic pulse) may still obscure the detectable ECAP signal from that informed stimulation pulse. In addition, regardless of the pulse width of the informed stimulation pulse, it may be beneficial to sense ECAP signals resulting from control stimulation pulses so that the informed stimulation pulses can have parameter values (e.g., amplitude, pulse width, frequency, pulse shape, electrode combination, etc.) that would otherwise interfere with the sensing of the resulting ECAP signal or the production of a detectable ECAP signal.

Although the technique of FIG. 4C is described for adjusting the amplitude of the informed stimulation pulses and the control stimulation pulses, other parameter values may be changed in other examples. For example, sensed ECAP signals may be used to increase or decrease the pulse width of the informed stimulation pulse and the control stimulation pulse to adjust the amount of charge delivered to the tissue to maintain consistent volume of neural activation. In other examples, electrode combinations may be adjusted in order to deliver different amounts of charge and modify the number of neurons being recruited by each informed stimulation pulse. In other examples, processing circuitry 214 may be configured to adjust the slew rate of the informed stimulation pulses and/or control stimulation pulses (e.g., the rate of change of the voltage and/or amplitude at the beginning and/or end of the pulse or each phase of the pulse) in response to a characteristic of the ECAP signal, such as the amplitude of recent ECAP amplitudes. For parameters other than amplitude, gain values may need to be determined that are specific for each type of parameter in order to appropriately adjust that type of parameter. Processing circuitry 214 may change one or more parameters defining the informed stimulation pulse and/or control stimulation pulse according to the process described here with respect to FIG. 4C. For example, the ECAP signal may be used to control multiple concurrent feedback mechanisms simultaneously for respective pulse parameters. In other examples, processing circuitry 214 may switch between two or more feedback mechanisms when processing circuitry 214 reaches a limit of adjustment for a specific parameter. For example, processing circuitry 214 may be configured to use a feedback control mechanism to adjust amplitude as long as the amplitude remains within a range (e.g., a range defined by the clinician) and then switch to a different feedback control mechanism to adjust a different parameter (e.g., pulse width or slew rate) of the informed stimulation pulses and/or control stimulation pulses in response to the amplitude exceeding the range.

Figure 5A:
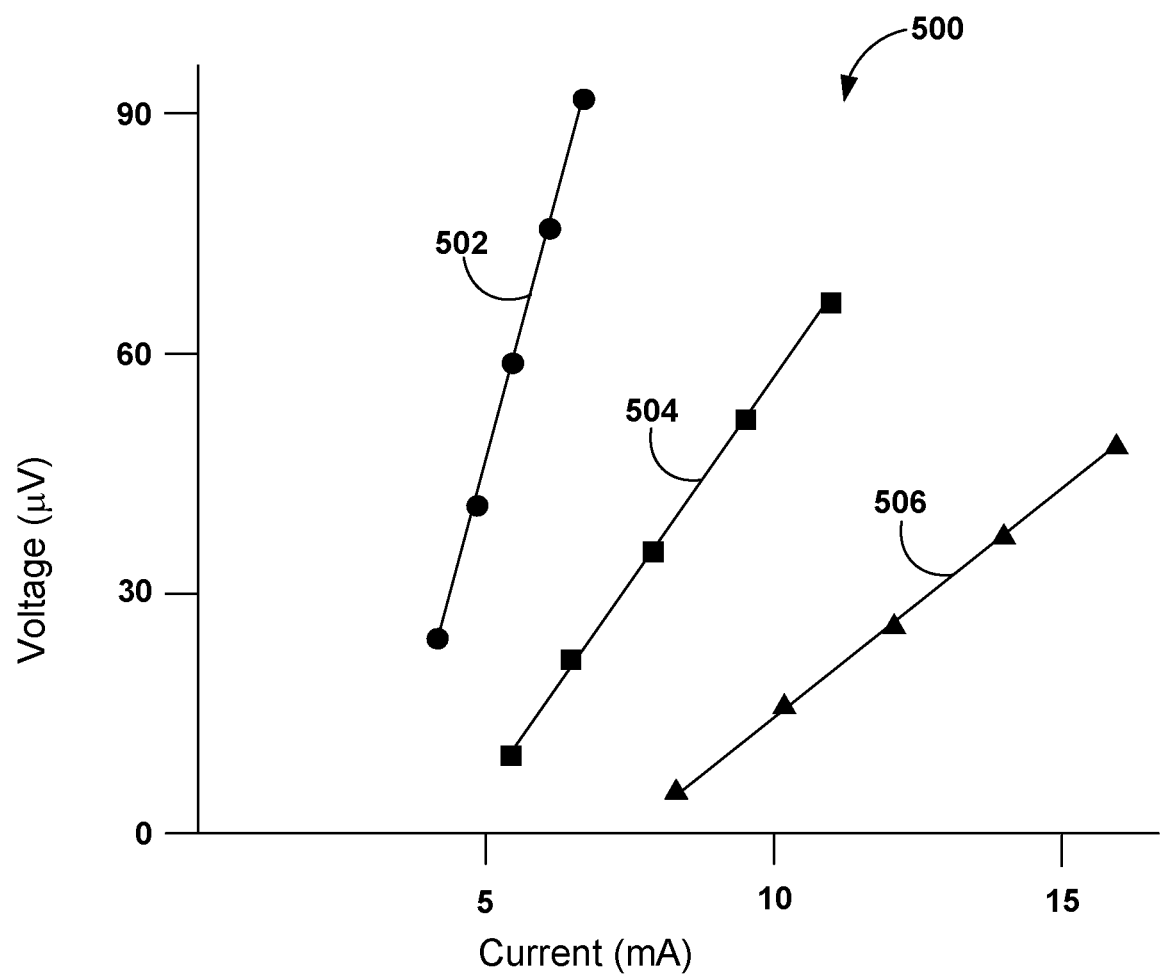
FIG. 5A is a graph of example growth curves of sensed ECAPs from respective stimulation pulse amplitudes at different postures.

FIG. 5A is a graph 500 of example growth curves 502, 504, and 506 of sensed ECAPs from respective stimulation pulse amplitudes at different postures. Graph 500 illustrates example characteristic values of ECAP signals 502, 504, and 506, the characteristic values shown as dots (growth curve 502), squares (growth curve 504), and triangles (growth curve 506) for respective different current amplitudes of stimulation pulses. A nerve tissue of a patient sometimes will not generate an ECAP response until a stimulation pulse amplitude reaches a threshold. As depicted in the example of FIG. 5A, the threshold is a current amplitude of approximately 4.5 mA for growth curve 502. As the current amplitude increases, a characteristic value (e.g., an amplitude in the example of FIG. 5A) of the ECAP response also increases approximately linearly. This linear relationship is shown by growth curves 502, 504, 506. The ECAP growth curve may vary for each patient based on the type of electrodes implanted, where the electrodes are implanted, the sensitivity of the patient's neurons to stimulation, neurological dysfunction, or other factors. Furthermore, as recognized by the techniques of the disclosure, the ECAP growth curves varies depending on the posture state of the patient.

While a patient is in a given posture state, sensed ECAPs may be detected for stimulation pulses with different current amplitudes. For example, each growth curve 502, 504, and 506 may represent the identified gain in ECAP amplitude for a given increase in pulse amplitude for a given single posture state, e.g., supine, prone, sitting, standing, left lateral recumbent (e.g., lying on the left side), or right lateral recumbent (e.g., lying on the right side). If a patient changes posture states, the growth curve may also change. This is because a distance between the electrodes of IMD 110 of FIG. 1 and the nerve tissue of patient 105 may increase or decrease as the patient changes posture. Therefore, when a patient changes posture states, e.g., supine to standing and standing to running, the corresponding growth curve can change as well. For example, changing from growth curve 502 to growth curve 504 and from growth curve 504 to growth curve 506 could be an example of a patient moving from supine to standing to running. In some examples, a patient may change posture states, but that change in posture state may not result in a change in the growth curve. This has the further effect that, for an electrical stimulation pulse delivered according to a fixed therapy parameter set, the electrical stimulation pulse may have an amplitude that is less than a threshold that evokes an ECAP response when the patient is in a first posture. Furthermore, the electrical stimulation pulse may be greater than a perception threshold of the patient when the patient is in a second posture, and may exceed a discomfort threshold of the patient when the patient is in a third posture.

The slope of the growth curves 502, 504, and 506 that linearly increase may be referenced as the "gain" herein, as it indicates the relationship between sensed ECAP amplitudes and pulse amplitudes. Put another way, the gain value may represent the slope of the growth curve of values of the characteristic of ECAP signals (e.g., an amplitude such as the N1-P2 amplitude or the amplitude of any peak of the ECAP signal) elicited from respective calibration stimulation pulses delivered to the patient and at least partially defined by different values of a stimulation parameter (e.g., current amplitude, voltage amplitude, or pulse width). For example, an IMD system as described herein may select a growth curve having a particular gain value that corresponds to a posture state of the patient. The gain value of the selected growth curve may be used to dynamically adjust pulse amplitude based on the sensed ECAP amplitudes. In some examples, the gain may be approximated for a patient based on historical data for similar patients. In other examples, the system may generate a custom growth curve and gain specific to the patient before starting therapy with the system. For example, a steeper growth curve may result in the system making larger adjustments to stimulation parameters of subsequent pulses for a given change in ECAP amplitude when compared to shallower growth curves.

Figure 5B:
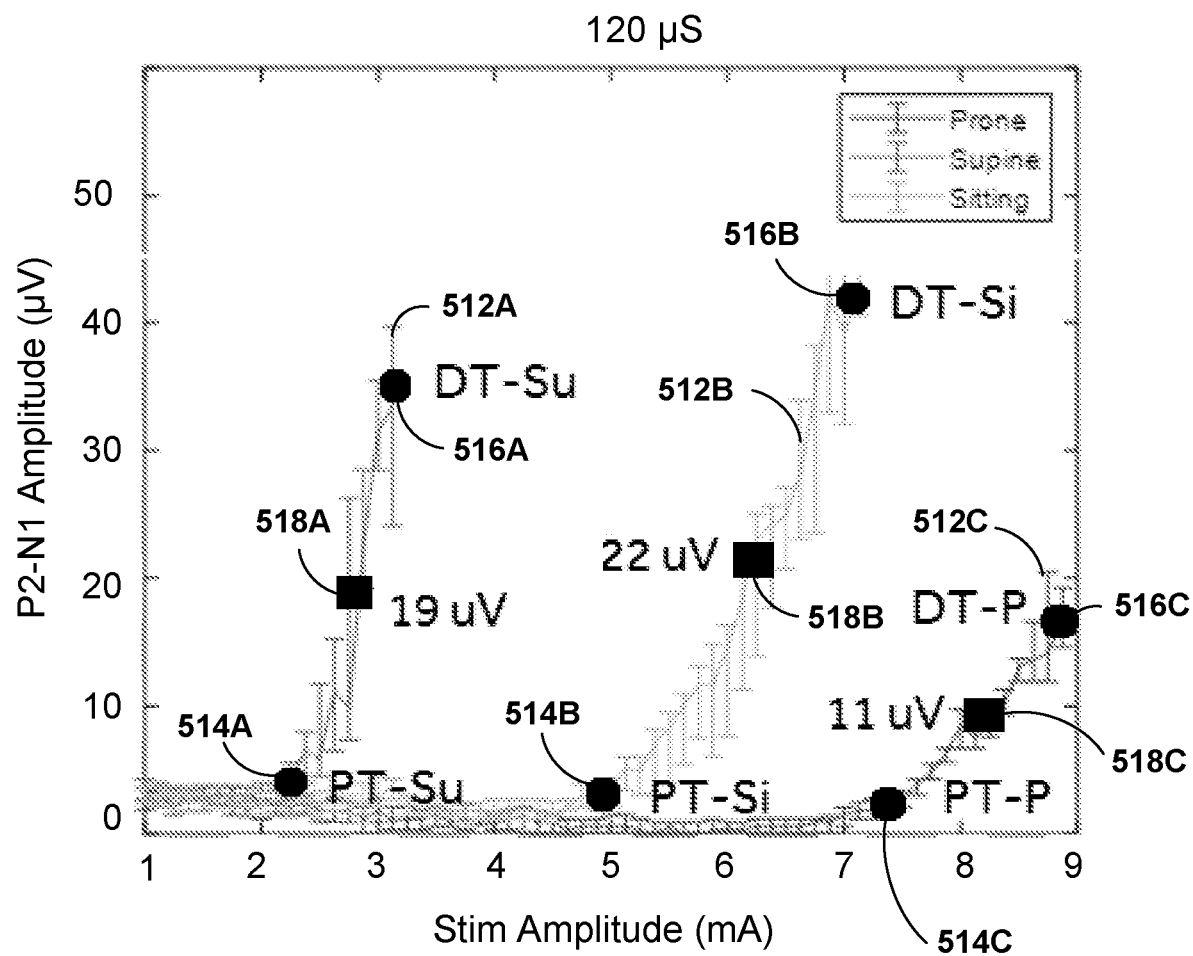
FIG. 5B is a graph of example growth curves of sensed ECAPs from respective stimulation pulse amplitudes at different postures.

FIG. 5B is a graph of example growth curves 512A-512C (collectively, "growth curves 512") of sensed ECAPs from respective stimulation pulse amplitudes at different postures. In the example of FIG. 5B, stimulation pulses of varying amplitude are delivered to a nerve tissue of a patient. Each growth curve 512 depicts a relationship of a characteristic value (e.g., an amplitude in the example of FIG. 5B) of an ECAP response of the nerve tissue of the patient to the amplitude of the stimulation pulse. The nerve tissue of the patient does not generate an ECAP response until the amplitude of the stimulation pulse exceeds a threshold. After the amplitude of the stimulation pulse exceeds the threshold, as the current amplitude increases, an amplitude of the ECAP response also increases approximately linearly. While FIG. 5B depicts a current amplitude relationship between the stimulation pulse and the amplitude of the ECAP response, stimulation therapy parameters other than current amplitude may also be used to elicit an ECAP response in the patient (e.g., voltage amplitude, pulse width, frequency, slew rate, duty cycle, etc.).

The ECAP responses of the patient to stimulation pulses may be used as a part of a neurostimulation feedback system to maintain a constant level of paresthesia in the patient. This constant level of paresthesia may be achieved by adapting the amplitude of a stimulation pulse (or other type of parameter) to approximate a target ECAP characteristic. A desired target ECAP characteristic for controlling the neurostimulation feedback system may vary as a function of posture. As described herein, a target ECAP characteristic may be selected dependent on a posture of the patient, or other transient patient conditions, such as sneezing, coughing, etc. A system as described herein may automatically select target ECAP characteristic of a growth curve specific to a sensed posture of the patient.

Each of growth curves 512 correspond to the same patient assuming a different posture. For example, growth curve 512A corresponds to the patient in a supine position, growth curve 512B corresponds to the patient in a sitting position, and growth curve 512C corresponds to the patient in a prone position. This is because as the patient changes posture, different positions of the body of the patient (e.g., standing, sitting, laying down) may cause the electrodes disposed along a spinal cord, e.g., leads 130 of IMD 110 of FIG. 1, to move slightly closer to or farther from the nerves of the target tissue of patient 105. Thus, for a stimulation pulse having the same therapy parameter set, the stimulation pulse may result in different volumes of neural activation depending on the posture of the patient.

Each of growth curves 512 exhibits a respective perception threshold 514A-514C (collectively, "perception thresholds 514"). The perception thresholds 514 correspond to a stimulation amplitude at a level at which the patient perceives the resulting ECAP response (e.g., as paresthesia, numbness, absence of pain, etc.). The perception thresholds 514 may be different for each patient. As depicted in FIG. 5B, each perception threshold 514A, 514B, 514C has a different value that corresponds to a different posture of the patient. Typically, a stimulation amplitude that is above the perception threshold 514 is desirable because this amplitude results in effective therapy to the patient.

Each of growth curves 512 further exhibits a respective discomfort threshold 516A-516C (collectively, "discomfort thresholds 516"). The discomfort thresholds 516 correspond to a stimulation amplitude at a level at which the patient experiences discomfort from the resulting ECAP response (e.g., as paresthesia, numbness, etc.). The discomfort thresholds 516 may be different for each patient. As depicted in FIG. 5B, each discomfort threshold 516A, 516B, 516C has a different value that corresponds to a different posture of the patient. Typically, a stimulation amplitude that is below the discomfort threshold 516 may be desirable because this amplitude avoids causing discomfort in the patient.

As discussed above, the study of perception thresholds 514 and discomfort thresholds 516 with ECAP responses suggests that a desired stimulation amplitude (or other stimulation parameter) varies as a function of posture. A target ECAP characteristic for stimulation therapy is a point between perception threshold 514 and discomfort threshold 516 of a growth curve 512 and varies depending on a posture of the patient. In some examples, the target ECAP characteristic is defined as midpoints 518A-518C (collectively, "midpoints 518") between perception thresholds 514 and discomfort thresholds 516 of growth curves 512. Although FIG. 5 depicts the target ECAP characteristic as a midpoint value 518 between a voltage amplitude of perception threshold 514 and a voltage amplitude of discomfort threshold 516, the target ECAP characteristic may be any value along the ECAP growth curve 512 between perception threshold 514 and discomfort threshold 516 that is preferable to the patient, or another characteristic of ECAP growth curve 512 other than voltage amplitude (e.g., such as current amplitude).

In accordance with the techniques of the disclosure, a medical device system senses a posture of the patient. In some examples, the posture of the patient is detected via accelerometry, stimulation artifact morphology, or a growth curve. The system selects a growth curve 512 that corresponds to the posture of the patient, and selects a target ECAP characteristic (e.g., such as midpoint 518) for the selected growth curve 512. For example, in response to detecting that patient 105 of FIG. 1 is sitting, IMD 110 selects growth curve 512B as a growth curve for defining the relationship between stimulation pulses and an ECAP response of patient 105. Further, IMD 110 selects midpoint 518B of growth curve 512B as a target ECAP characteristic for controlling the amplitude of stimulation pulses delivered to patient 105 as described above with respect to FIGS. 4A-4C.

In response to detecting that patient 105 of FIG. 1 has transitioned from sitting to a supine position, IMD 110 selects growth curve 512A as a growth curve for defining the relationship between stimulation pulses and an ECAP response of patient 105. Further, IMD 110 selects midpoint 518A of growth curve 512A as a target ECAP characteristic for controlling the amplitude of stimulation pulses delivered to patient 105. The system may also smoothly transition from using midpoint 518B as the target ECAP characteristic to midpoint 518A as the target ECAP characteristic to avoid abrupt changes in sensation for the patient.

Figure 6:
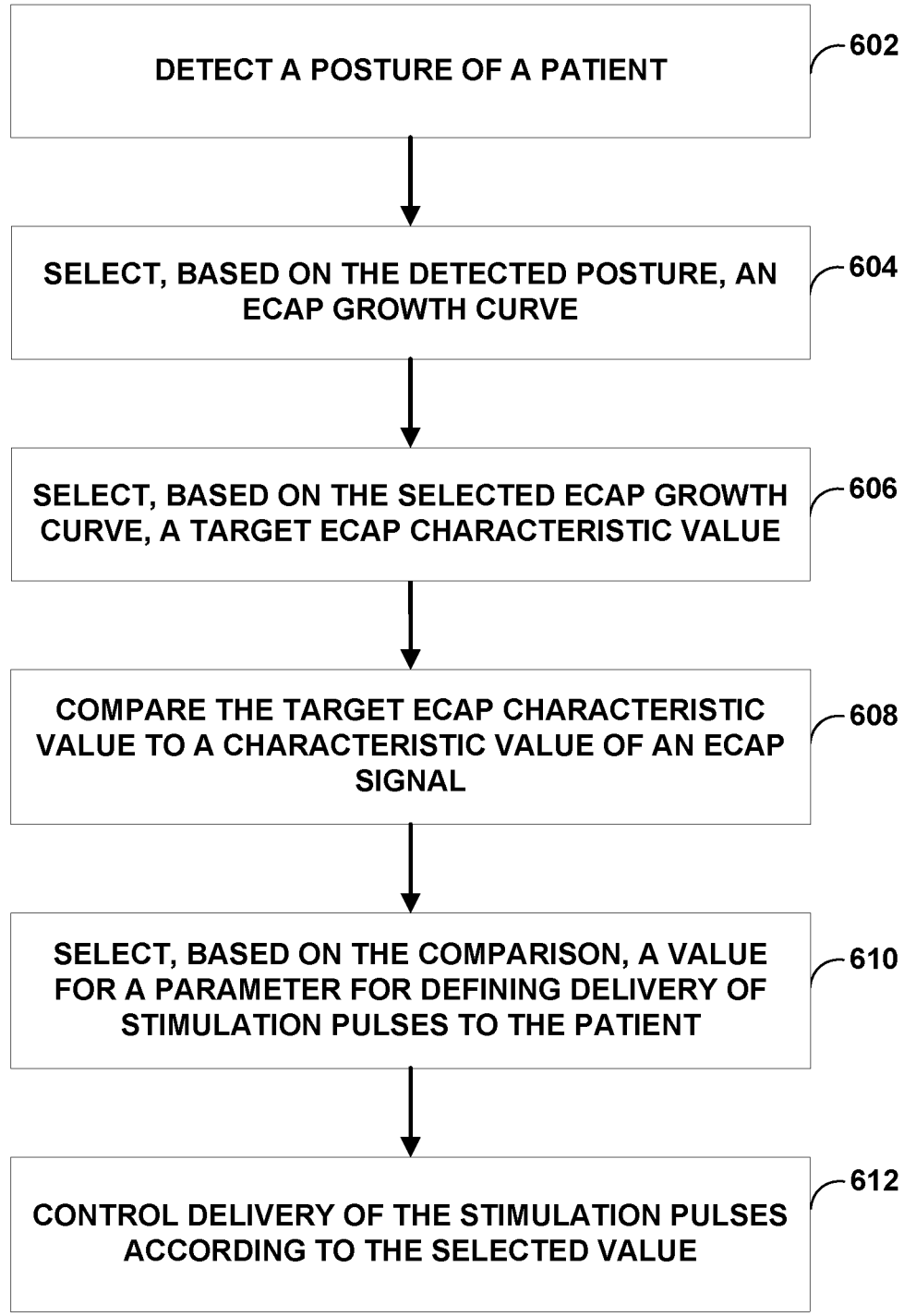
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to IMD 200 of FIG. 2A. As described by the operation of FIG. 6, IMD 200 may dynamically adjust an amplitude (or other parameter defining stimulation pulses) of electrical stimulation pulses based on a gain value representing the patient sensitivity to stimulation. As described herein, processing circuitry 214 of IMD 200 may select a gain value of an ECAP growth curve, the ECAP growth curve associated with a current posture of the patient. Processing circuitry 214 may control stimulation generator 211 to deliver a stimulation pulse to a patient. Processing circuitry 214 may then control sensing circuitry 212 to sense an ECAP signal elicited by the stimulation pulse and then identify a characteristic of the ECAP signal (e.g., an amplitude of the ECAP signal). Processing circuitry 214 may then determine, based on the characteristic of the ECAP signal and a gain value, a stimulation parameter value (e.g., an amplitude, pulse width value, pulse frequency value, and/or slew rate value) that at least partially defines a subsequent stimulation pulse. Processing circuitry 214 may then control stimulation generator 211 to deliver the subsequent stimulation pulse according to the determined stimulation parameter value.

As shown in the example of FIG. 6, sensor 216 senses a posture and/or patient activity of patient 105 of FIG. 1 (602). Sensor 216 may include one or more sensing elements that sense values of a respective patient parameter. Sensor 216 may include one or more accelerometers or other types of sensors. Sensor 216 senses a posture of a patient and/or patient activity. The detected posture of the patient may include one or more of a standing position, an upright position, a sitting position, a prone position, a supine position, a right lateral position, a left lateral position, etc. In other examples, a patient may input the current posture using a user interface in communication with IMD 200.

Processing circuitry 214 then selects, based on the detected posture, an ECAP growth curve (604). For example, ECAP growth curves 223 stored by memory 215 may include a plurality of ECAP growth curves that correspond to respective postures of a plurality of postures of patient 105. Processing circuitry 214 selects the ECAP growth curve of ECAP growth curves 223 that corresponds to the detected posture of patient 105.

In some examples, processing circuitry 214 selects, based on the selected ECAP growth curve, a target ECAP characteristic value (606). For example, processing circuitry 214 selects a target ECAP characteristic value along the selected ECAP growth curve. In some examples, the target ECAP characteristic value is a value of an ECAP characteristic along the selected ECAP growth curve that corresponds to a value of an amplitude (or other parameter) of a control stimulation pulse that evokes an ECAP response greater than a perception threshold of the patient. In some examples, the target ECAP characteristic value is a value of an ECAP characteristic along the selected ECAP growth curve that corresponds to a value of an amplitude (or other parameter) of a control stimulation pulse that evokes an ECAP response less than a discomfort threshold of the patient.

In some examples, the target ECAP characteristic value is between a value of an ECAP characteristic along the selected ECAP growth curve that corresponds to a value of an amplitude (or other parameter) of a control stimulation pulse that evokes an ECAP response greater than a perception threshold of the patient and a value of an ECAP characteristic along the selected ECAP growth curve that corresponds to a value of an amplitude (or other parameter) of a control stimulation pulse that evokes an ECAP response less than a discomfort threshold of the patient. For example, the target ECAP characteristic value is a midpoint between a value of an ECAP characteristic along the selected ECAP growth curve that corresponds to a value of an amplitude (or other parameter) of a control stimulation pulse that evokes an ECAP response greater than a perception threshold of the patient and a value of an ECAP characteristic along the selected ECAP growth curve that corresponds to a value of an amplitude (or other parameter) of a control stimulation pulse that evokes an ECAP response less than a discomfort threshold of the patient.

Values for each of the amplitude (or other parameter) of the control stimulation pulse that evokes the ECAP response corresponding to the perception threshold of the patient and the amplitude (or other parameter) of the control stimulation pulse that evokes the ECAP response corresponding to the perception threshold of the patient may be determined by a clinician during initial calibration of IMD 200. The target ECAP characteristic value may essentially represent a reference distance between the stimulation electrodes and the target neurons (e.g., the spinal cord for the case of SCS) when patient 105 is in a posture that corresponds to the selected ECAP growth curve. In the foregoing examples, processing circuitry 214 selects an ECAP growth curve that corresponds to a detected posture of the patient, and selects a target ECAP characteristic value that lies along the selected ECAP growth curve. In other examples, processing circuitry 214 may directly select a target ECAP characteristic value based on the detected posture instead of first selecting a growth curve.

Processing circuitry 214 controls stimulation generator 211 to deliver a control stimulation pulse to patient 105 and senses an ECAP signal elicited by the control pulse. Processing circuitry 214 compares the target ECAP characteristic value to a characteristic value of the sensed ECAP signal elicited by the control pulse (608). Processing circuitry 214 selects, based on the comparison of the target ECAP characteristic value to the characteristic value of the sensed ECAP signal elicited by the control pulse, a value for a parameter for defining delivery of the stimulation pulses to patient 105 (610).

Processing circuitry 214 then controls stimulation generator 211 to deliver the stimulation pulses according to the selected value of the stimulation parameter (612). For example, processing circuitry 214 controls stimulation generator 211 to deliver a stimulation pulse to patient 105. Processing circuitry 214 senses an ECAP evoked by the stimulation pulse. For each sensed ECAP, processing circuitry 214 measures a characteristic value of the ECAP signal and compares the characteristic value of the ECAP signal to the target ECAP characteristic value. Processing circuitry 214 adjusts an amplitude (or other parameter) of the stimulation pulse so as to reduce a difference between the characteristic value of the ECAP signal and the target ECAP characteristic value. Processing circuitry 214 controls stimulation generator 211 to deliver the adjusted stimulation pulses according to the new amplitude.

Accordingly, the techniques of the disclosure may enable IMD 200 to maintain a consistent volume of neural activation by adjusting the one or more stimulation parameters of the stimulation pulses in proportion to an ECAP growth curve that itself is a function of the sensed posture of the patient. Therefore, the techniques of the disclosure may enable for an IMD to provide electrical stimulation therapy that delivers a consistent level of therapeutic electrical stimulation to the patient, despite changes in the posture of the patient, changes in the position of the leads of the IMD over time, or changes in the biochemistry of the patient. Accordingly, the techniques of the disclosure may provide higher therapeutic efficacy over conventional electrical stimulation systems.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   selecting, by one or more processors and based on a detected posture from a plurality of postures of a patient, an evoked compound action potential (ECAP) growth curve of a plurality of ECAP growth curves, wherein each ECAP growth curve of the plurality of ECAP growth curves is associated with at least one posture of the plurality of postures, and wherein each ECAP growth curve of the plurality of ECAP growth curves defines a relationship between a parameter defining delivery of one or more stimulation pulses to the patient and a characteristic of an ECAP signal elicited by a control stimulation pulse;
   selecting, by the one or more processors and based on the selected ECAP growth curve, a value of a target ECAP characteristic;
   comparing the value of the target ECAP characteristic to a value of the characteristic of the ECAP signal elicited by the control stimulation pulse;
   selecting, based on the comparison, a value for the parameter defining delivery of the one or more stimulation pulses to the patient; and
   controlling, by the one or more processors, delivery of the one or more stimulation pulses according to the selected value for the parameter.

2. The method of claim 1, further comprising sensing, by sensing circuitry, the ECAP signal elicited by the control stimulation pulse.

3. The method of claim 2,
   wherein the one or more stimulation pulses comprise one or more informed stimulation pulses defined by a first set of stimulation parameters different than a second set of parameters that define the control stimulation pulse, the first set of stimulation parameters comprising the selected value for the parameter,
   wherein selecting, based on the comparison, the value for the parameter defining delivery of the one or more stimulation pulses to the patient comprises adjusting, based on the comparison, a value for a parameter defining delivery of one or more informed stimulation pulses to the patient, and
   wherein controlling delivery of the one or more stimulation pulses according to the selected value for the parameter comprises controlling delivery of the one or more informed stimulation pulses according to the adjusted value for the parameter.

4. The method of claim 1, wherein selecting, based on the selected ECAP growth curve, the value of the target ECAP characteristic comprises:
   determining a perception threshold of the patient on the selected ECAP growth curve; and
   selecting a value for the target ECAP characteristic that is greater than the perception threshold.

5. The method of claim 1, wherein selecting, based on the selected ECAP growth curve, the value of the target ECAP characteristic comprises:
   determining a perception threshold of the patient on the selected ECAP growth curve;
   determining a discomfort threshold of the patient on the selected ECAP growth curve; and
   selecting a value for the target ECAP characteristic that is greater than the perception threshold and less than the discomfort threshold.

6. The method of claim 5, wherein selecting the value for the target ECAP characteristic that is greater than the perception threshold and less than the discomfort threshold comprises selecting a value for the target ECAP characteristic that is a midpoint between the perception threshold and the discomfort threshold on the selected ECAP growth curve.

7. The method of claim 1,
   wherein comparing the value of the target ECAP characteristic to the value of the characteristic of the ECAP signal elicited by the control stimulation pulse comprises one of:

determining that the value of the target ECAP characteristic is greater than the value of the characteristic of the ECAP signal elicited by the control stimulation pulse, wherein selecting, based on the comparison, the value for the parameter defining delivery of the one or more stimulation pulses to the patient comprises increasing the value for the parameter defining delivery of the one or more stimulation pulses to the patient; or determining that the value of the target ECAP characteristic is less than the value of the characteristic of the ECAP signal elicited by the control stimulation pulse, wherein selecting, based on the comparison, the value for the parameter defining delivery of the one or more stimulation pulses to the patient comprises decreasing the value for the parameter defining delivery of the one or more stimulation pulses to the patient.

8. The method of claim 1, wherein the parameter defining delivery of the one or more stimulation pulses comprises one of a current amplitude, a voltage amplitude, a pulse width, or a frequency of the one or more stimulation pulses.

9. The method of claim 1, wherein the characteristic of the ECAP signal elicited by the control stimulation pulse comprises one of a current amplitude or a voltage amplitude of the ECAP signal elicited by the control stimulation pulse.

10. The method of claim 1, further comprising detecting the detected posture of the plurality of postures of the patient by detecting a change from a first posture of the plurality of postures of the patient to a second posture of the plurality of postures of the patient, wherein selecting, based on the detected posture, the ECAP growth curve of the plurality of ECAP growth curves comprises switching, based on the detected change from the first posture to the second posture, from a first ECAP growth curve of the plurality of ECAP growth curves to a second ECAP growth curve of the plurality of ECAP growth curves, wherein the first ECAP growth curve is associated with the first posture of the patient and the second ECAP growth curve is associated with the second posture of the patient, wherein selecting, based on the selected ECAP growth curve, the value of the target ECAP characteristic comprises switching from selecting a first value of a first target ECAP characteristic based on the first ECAP growth curve to selecting a second value of a second target ECAP characteristic based on the second ECAP growth curve, wherein comparing the value of the target ECAP characteristic to the value of the characteristic of the ECAP signal elicited by the control stimulation pulse comprises switching from comparing the first value of the first target ECAP characteristic to the value of the characteristic of the ECAP signal elicited by the control stimulation pulse to comparing the second value of the second target ECAP characteristic to the value of the characteristic of the ECAP signal elicited by the control stimulation pulse, wherein selecting, based on the comparison, the value for the parameter defining delivery of the one or more stimulation pulses to the patient comprises switching from selecting a first value for the parameter defining delivery of the one or more stimulation pulses to the patient based on the comparison of the first value of the first target ECAP characteristic to the value of the characteristic of the ECAP signal elicited by the control stimulation pulse to selecting a second value for the parameter defining delivery of the one or more stimulation pulses to the patient based on the comparison of the second value of the second target ECAP characteristic to the value of the characteristic of the ECAP signal elicited by the control stimulation pulse, and wherein controlling delivery of the one or more stimulation pulses according to the selected value for the parameter comprises switching from controlling delivery of the one or more stimulation pulses according to the first value for the parameter to controlling delivery of the one or more stimulation pulses according to the second value for the parameter.

11. A system comprising:
a medical device comprising therapy delivery circuitry configured to deliver therapy to a patient; and
processing circuitry configured to:
select, based on a detected posture from a plurality of postures of a patient, an evoked compound action potential (ECAP) growth curve of a plurality of ECAP growth curves,
wherein each ECAP growth curve of the plurality of ECAP growth curves is associated with at least one posture of the plurality of postures, and
wherein each ECAP growth curve of the plurality of ECAP growth curves defines a relationship between a parameter defining delivery of one or more stimulation pulses to the patient and a characteristic of an ECAP signal elicited by a control stimulation pulse;
select, based on the selected ECAP growth curve, a value of a target ECAP characteristic;
compare the value of the target ECAP characteristic to a value of the characteristic of the ECAP signal elicited by the control stimulation pulse;
select, based on the comparison, a value for the parameter defining delivery of the one or more stimulation pulses to the patient; and
control the therapy delivery circuitry of the medical device to deliver the one or more stimulation pulses according to the selected value for the parameter.

12. The system of claim 11, further comprising sensing circuitry configured to sense, via one or more electrodes coupled to the medical device, the ECAP signal elicited by the control stimulation pulse.

13. The system of claim 12,
wherein the one or more stimulation pulses comprise one or more informed stimulation pulses defined by a first set of stimulation parameters different than a second set of parameters that define the control stimulation pulse, the first set of stimulation parameters comprising the selected value for the parameter,
wherein to select, based on the comparison, the value for the parameter defining delivery of the one or more stimulation pulses to the patient, the processing circuitry is further configured to adjust, based on the comparison, a value for a parameter defining delivery of one or more informed stimulation pulses to the patient, and
wherein to control the therapy delivery circuitry of the medical device to deliver the one or more stimulation pulses according to the selected value for the parameter, the processing circuitry is further configured to control the therapy delivery circuitry of the medical device to deliver the one or more informed stimulation pulses according to the adjusted value for the parameter.

14. The system of claim 11, wherein to select, based on the selected ECAP growth curve, the value of the target ECAP characteristic, the processing circuitry is further configured to:
   determine a perception threshold of the patient on the selected ECAP growth curve; and
   select a value for the target ECAP characteristic that is greater than the perception threshold.

15. The system of claim 13, wherein to select, based on the selected ECAP growth curve, the value of the target ECAP characteristic, the processing circuitry is further configured to:
   determine a perception threshold of the patient on the selected ECAP growth curve;
   determine a discomfort threshold of the patient on the selected ECAP growth curve; and
   select a value for the target ECAP characteristic that is greater than the perception threshold and less than the discomfort threshold.

16. The system of claim 15, wherein to select the value for the target ECAP characteristic that is greater than the perception threshold and less than the discomfort threshold, the processing circuitry is further configured to select a value for the target ECAP characteristic that is a midpoint between the perception threshold and the discomfort threshold on the selected ECAP growth curve.

17. The system of claim 11, wherein the processing circuitry is configured to compare the value of the target ECAP characteristic to the value of the characteristic of the ECAP signal elicited by the control stimulation pulse by at least one of:
   determining that the value of the target ECAP characteristic is greater than the value of the characteristic of the ECAP signal elicited by the control stimulation pulse, wherein the processing circuitry is configured to select, based on the comparison, the value for the parameter defining delivery of the one or more stimulation pulses to the patient by at least increasing the value for the parameter defining delivery of the one or more stimulation pulses to the patient; or
   determining that the value of the target ECAP characteristic is less than the value of the characteristic of the ECAP signal elicited by the control stimulation pulse, wherein the processing circuitry is configured to select, based on the comparison, the value for the parameter defining delivery of the one or more stimulation pulses to the patient by at least decreasing the value for the parameter defining delivery of the one or more stimulation pulses to the patient.

18. The system of claim 11, wherein the characteristic of the ECAP signal elicited by the control stimulation pulse comprises one of a current amplitude or a voltage amplitude of the ECAP signal elicited by the control stimulation pulse.

19. The system of claim 11, further comprising one or more sensors, and wherein the processing circuitry is configured to detect, via the one or more sensors, the detected posture of the plurality of postures of the patient.

20. A non-transitory, computer-readable medium comprising instructions that, when executed, cause processing circuitry of a medical device to:
   select, based on a detected posture from a plurality of postures of a patient, an evoked compound action potential (ECAP) growth curve of a plurality of ECAP growth curves,
      wherein each ECAP growth curve of the plurality of ECAP growth curves is associated with at least one posture of the plurality of postures, and
      wherein each ECAP growth curve of the plurality of ECAP growth curves defines a relationship between a parameter defining delivery of one or more stimulation pulses to the patient and a characteristic of an ECAP signal elicited by a control stimulation pulse;
   select, based on the selected ECAP growth curve, a value of a target ECAP characteristic;
   compare the value of the target ECAP characteristic to a value of the characteristic of the ECAP signal elicited by the control stimulation pulse;
   select, based on the comparison, a value for the parameter defining delivery of the one or more stimulation pulses to the patient; and
   control delivery of the one or more stimulation pulses according to the selected value for the parameter.

* * * * *